(12) United States Patent
Li

(10) Patent No.: US 10,302,263 B2
(45) Date of Patent: May 28, 2019

(54) SCENTED IMITATION CANDLE DEVICE

(71) Applicant: Xiaofeng Li, Shenzhen (CN)

(72) Inventor: Xiaofeng Li, Shenzhen (CN)

( * ) Notice: Subject to any disclaimer, the term of this patent is extended or adjusted under 35 U.S.C. 154(b) by 0 days.

(21) Appl. No.: 15/886,781

(22) Filed: Feb. 1, 2018

(65) Prior Publication Data

US 2018/0292058 A1 Oct. 11, 2018

(51) Int. Cl.
| | | |
|---|---|---|
| *F21S 10/04* | (2006.01) | |
| *F21S 9/02* | (2006.01) | |
| *F21S 6/00* | (2006.01) | |
| *A61L 9/03* | (2006.01) | |
| *F21W 121/00* | (2006.01) | |
| *F21Y 115/10* | (2016.01) | |

(52) U.S. Cl.
CPC ............. *F21S 10/046* (2013.01); *A61L 9/03* (2013.01); *F21S 6/001* (2013.01); *F21S 9/02* (2013.01); *A61L 2209/111* (2013.01); *A61L 2209/12* (2013.01); *A61L 2209/133* (2013.01); *A61L 2209/135* (2013.01); *F21W 2121/00* (2013.01); *F21Y 2115/10* (2016.08)

(58) Field of Classification Search
CPC . F21S 10/046; F21S 6/001; F21S 9/02; A61L 9/03
See application file for complete search history.

(56) References Cited

U.S. PATENT DOCUMENTS

| | | |
|---|---|---|
| 782,156 A | 2/1905 | Meeker |
| 817,772 A | 4/1906 | Helmer |
| 1,507,371 A | 8/1924 | Goodridge |
| 1,842,167 A | 1/1932 | Hall |
| 1,955,042 A | 4/1934 | Work |
| D102,561 S | 12/1936 | Lamb |
| 2,435,811 A | 2/1948 | Waters |
| 2,932,351 A | 6/1958 | Bried |
| 2,976,450 A | 3/1961 | Benoliel |
| 2,984,032 A | 5/1961 | Cornell |
| 3,233,093 A | 2/1966 | Gerlat |
| 3,384,774 A | 5/1968 | English |

(Continued)

FOREIGN PATENT DOCUMENTS

| | | |
|---|---|---|
| CN | 1030823 | 2/1989 |
| CN | 2483103 | 3/2002 |

(Continued)

OTHER PUBLICATIONS

U.S. Appl. No. 15/197,354, filed Jun. 29, 2016, Li.

(Continued)

*Primary Examiner* — Regina M Yoo
(74) *Attorney, Agent, or Firm* — Perkins Coie LLP

(57) ABSTRACT

Methods, systems, and devices relating to an electronic scented candle that is convenient to use and enables rapid generation and dissipation of scented materials are described. One electronic candle device includes a shell that has a through hole, a flame element protruding through the through hole, an installation lid including a locking base to allow removable coupling of a fragrance container, a scent chamber including a locking clip, a first channel, a second channel, a third channel, and a fourth channel. The scent chamber is removably coupled to the locking base by the locking clip, and an air pump provided to supply pressurized air.

20 Claims, 35 Drawing Sheets

(56) References Cited

U.S. PATENT DOCUMENTS

| | | | |
|---|---|---|---|
| 3,425,157 | A | 2/1969 | Hartsock |
| 3,514,660 | A | 5/1970 | Kopelman |
| 3,603,013 | A | 9/1971 | Gardiner |
| 3,639,749 | A | 2/1972 | Beckman |
| 3,681,588 | A | 8/1972 | Lee |
| 3,814,973 | A | 6/1974 | Thouret et al. |
| 3,890,085 | A | 6/1975 | Andeweg |
| 4,026,544 | A | 5/1977 | Plambeck et al. |
| 4,067,111 | A | 1/1978 | Truitt |
| 4,328,534 | A | 5/1982 | Abe |
| 4,477,249 | A | 10/1984 | Ruzek et al. |
| 4,550,363 | A | 10/1985 | Sandell |
| 4,551,794 | A | 11/1985 | Sandell |
| 4,617,614 | A | 10/1986 | Lederer |
| 4,728,871 | A | 3/1988 | Andrews |
| 4,777,571 | A | 10/1988 | Morgan |
| 4,866,580 | A | 9/1989 | Blackerby |
| 4,965,707 | A | 10/1990 | Butterfield |
| 4,968,487 | A | 11/1990 | Yamamoto |
| 5,072,208 | A | 12/1991 | Christensen |
| 5,097,180 | A | 3/1992 | Ignon et al. |
| 5,152,602 | A | 10/1992 | Boschetto |
| 5,381,325 | A | 1/1995 | Messana |
| 5,707,282 | A | 1/1998 | Clements et al. |
| 5,924,784 | A | 7/1999 | Chliwnyj et al. |
| 6,198,229 | B1 | 3/2001 | McCloud |
| 6,241,362 | B1 | 6/2001 | Morrison |
| 6,257,755 | B1 | 7/2001 | Sevelle |
| 6,302,555 | B1 | 10/2001 | Bristow |
| 6,312,137 | B1 | 11/2001 | Hsieh |
| 6,454,425 | B1 | 9/2002 | Lin |
| 6,461,011 | B1 | 10/2002 | Harrison |
| 6,511,219 | B2 | 1/2003 | Sevelle |
| D486,924 | S | 2/2004 | Skradski et al. |
| 6,688,752 | B2 | 2/2004 | Moore |
| 6,712,493 | B2 | 3/2004 | Tell et al. |
| 6,757,487 | B2 | 6/2004 | Martin et al. |
| 6,781,270 | B2 | 8/2004 | Long |
| 6,953,401 | B2 | 10/2005 | Starr |
| 6,955,440 | B2 | 10/2005 | Niskanen |
| 6,966,665 | B2 | 11/2005 | Limburg et al. |
| 7,029,146 | B2 | 4/2006 | Kitchen |
| 7,066,637 | B2 | 6/2006 | Nozawa |
| 7,080,472 | B2 | 7/2006 | Schroeter et al. |
| 7,080,762 | B1 | 7/2006 | Schwartz et al. |
| 7,083,315 | B2 | 8/2006 | Hansler et al. |
| 7,093,949 | B2 | 8/2006 | Hart et al. |
| 7,111,421 | B2 | 9/2006 | Corry et al. |
| 7,118,243 | B2 | 10/2006 | McCavit et al. |
| 7,125,142 | B2 | 10/2006 | Wainwright |
| 7,159,994 | B2 | 1/2007 | Schnuckle et al. |
| D545,458 | S | 6/2007 | Jensen |
| 7,261,455 | B2 | 8/2007 | Schnuckle et al. |
| 7,300,179 | B1 | 11/2007 | LaDuke et al. |
| 7,305,783 | B2 | 12/2007 | Mix et al. |
| D567,993 | S | 4/2008 | Shiu |
| 7,350,720 | B2 | 4/2008 | Jaworksi |
| 7,360,935 | B2 | 4/2008 | Jensen et al. |
| D576,317 | S | 9/2008 | Jensen |
| D589,176 | S | 3/2009 | Huang et al. |
| D599,491 | S | 9/2009 | Luo |
| 7,633,232 | B2 | 12/2009 | Wong |
| 7,686,471 | B2 | 3/2010 | Reichow |
| 7,695,171 | B2 | 4/2010 | Lederer |
| 7,723,899 | B2 | 5/2010 | Blandino |
| 7,784,959 | B2 | 8/2010 | Yang |
| 7,824,627 | B2 | 11/2010 | Michaels et al. |
| 7,828,462 | B2 | 11/2010 | Jensen et al. |
| 7,837,355 | B2 | 11/2010 | Schnuckle |
| 8,070,319 | B2 | 12/2011 | Schnuckle et al. |
| 8,081,872 | B2 | 12/2011 | Wang |
| 8,132,936 | B2 | 3/2012 | Patton et al. |
| 8,210,708 | B2 | 7/2012 | Negron |
| 8,235,558 | B1 | 8/2012 | Lauer |
| 8,256,935 | B1 | 9/2012 | Cullimore et al. |
| 8,342,712 | B2 | 1/2013 | Patton |
| 8,412,029 | B2 | 4/2013 | Browder |
| 8,454,190 | B2 | 6/2013 | Negron |
| 8,534,869 | B2 | 9/2013 | Patton et al. |
| 8,579,461 | B2 | 11/2013 | Fournier |
| 8,628,223 | B2 | 1/2014 | Kwok |
| 8,696,166 | B2 | 4/2014 | Patton et al. |
| 8,789,986 | B2 | 7/2014 | Li |
| 8,878,442 | B2 | 11/2014 | Lu |
| 8,894,261 | B2 | 11/2014 | Chen |
| 8,926,137 | B2 | 1/2015 | Li |
| 8,960,975 | B2 | 2/2015 | Yang |
| 8,998,461 | B2 | 4/2015 | Gutstein et al. |
| D729,424 | S | 5/2015 | Li |
| 9,033,533 | B2 | 5/2015 | Li |
| 9,033,553 | B2 | 5/2015 | Li |
| 9,052,078 | B2 | 6/2015 | Sheng |
| 9,068,706 | B2 | 6/2015 | Fournier |
| D739,573 | S | 9/2015 | Li |
| 9,133,992 | B2 | 9/2015 | Lee |
| D744,128 | S | 11/2015 | Li |
| 9,185,199 | B2 | 11/2015 | Zurek |
| D748,298 | S | 1/2016 | Li |
| 9,322,523 | B2 | 4/2016 | Patton |
| D757,306 | S | 5/2016 | Li |
| D757,335 | S | 5/2016 | Li |
| D757,336 | S | 5/2016 | Li |
| D757,337 | S | 5/2016 | Li |
| 9,335,014 | B2 | 5/2016 | Li |
| D759,858 | S | 6/2016 | Li |
| D759,879 | S | 6/2016 | Li |
| D759,880 | S | 6/2016 | Li |
| D760,405 | S | 6/2016 | Li |
| D760,422 | S | 6/2016 | Li |
| D760,423 | S | 6/2016 | Li |
| D760,424 | S | 6/2016 | Li |
| 9,360,181 | B2 | 6/2016 | Li |
| 9,366,402 | B2 | 6/2016 | Li |
| 9,371,972 | B2 | 6/2016 | Li |
| 9,371,973 | B2 | 6/2016 | Li |
| D763,479 | S | 8/2016 | Li |
| D767,799 | S | 9/2016 | Li |
| D767,810 | S | 9/2016 | Li |
| 9,447,938 | B2 | 9/2016 | Li |
| D774,474 | S | 12/2016 | Li |
| D774,478 | S | 12/2016 | Li |
| 9,512,971 | B2 | 12/2016 | Li |
| 9,518,710 | B2 | 12/2016 | Li |
| 9,523,471 | B2 | 12/2016 | Li |
| 9,551,470 | B2 | 1/2017 | Li |
| 9,572,236 | B2 | 2/2017 | Patton |
| 9,574,748 | B2 | 2/2017 | Dong |
| 9,585,980 | B1 | 3/2017 | Li |
| 9,591,727 | B2 | 3/2017 | Kim |
| 9,605,824 | B1 | 3/2017 | Li |
| 9,625,112 | B2 | 4/2017 | Li |
| D789,570 | S | 6/2017 | Li |
| D790,749 | S | 6/2017 | Li |
| D791,391 | S | 7/2017 | Li |
| D791,392 | S | 7/2017 | Li |
| D792,634 | S | 7/2017 | Li |
| 9,702,517 | B2 | 7/2017 | Patton |
| D795,735 | S | 8/2017 | Li |
| 9,739,432 | B2 | 8/2017 | Li |
| 9,752,740 | B1 | 9/2017 | Li |
| D800,929 | S | 10/2017 | Li |
| D802,180 | S | 11/2017 | Li |
| 9,810,388 | B1 | 11/2017 | Li |
| 9,860,953 | B2 | 1/2018 | Li |
| 9,869,439 | B2 | 1/2018 | Li |
| 2013/0223043 | A1* | 8/2013 | Ray ............... F21V 33/00 362/96 |
| 2016/0290580 | A1 | 10/2016 | Li |

(56) References Cited

U.S. PATENT DOCUMENTS

| | | |
|---|---|---|
| 2017/0191632 A1 | 7/2017 | Li |
| 2017/0307223 A1 | 10/2017 | Li |

FOREIGN PATENT DOCUMENTS

| | | |
|---|---|---|
| CN | 2551859 | 5/2003 |
| CN | 2562059 Y | 7/2003 |
| CN | 1530142 A | 9/2004 |
| CN | 1646177 A | 7/2005 |
| CN | 2854329 Y | 1/2007 |
| CN | 2888274 Y | 4/2007 |
| CN | 200940808 Y | 8/2007 |
| CN | 201011621 Y | 1/2008 |
| CN | 201059432 Y | 5/2008 |
| CN | 201093300 | 7/2008 |
| CN | 201103952 Y | 8/2008 |
| CN | 201159425 Y | 12/2008 |
| CN | 101408284 A | 4/2009 |
| CN | 201235095 Y | 5/2009 |
| CN | 201418887 Y | 3/2010 |
| CN | 201533921 U | 7/2010 |
| CN | 101865413 A | 10/2010 |
| CN | 201643048 U | 11/2010 |
| CN | 102147095 A | 8/2011 |
| CN | 102748589 A | 10/2012 |
| CN | 203131550 | 8/2013 |
| CN | 203273670 U | 11/2013 |
| CN | 203442498 U | 2/2014 |
| CN | 203517611 U | 4/2014 |
| CN | 203571618 U | 4/2014 |
| CN | 104048246 | 9/2014 |
| CN | 104089241 | 10/2014 |
| CN | 203940346 | 11/2014 |
| CN | 204268356 | 4/2015 |
| DE | 1489617 A1 | 5/1969 |
| DE | 212011100014 U1 | 4/2012 |
| DE | 202015000490 U1 | 3/2013 |
| DE | 102012206988 A1 | 10/2013 |
| DE | 202013012047 U1 | 2/2015 |
| DE | 202015102274 U1 | 5/2015 |
| EP | 138786 A1 | 4/1985 |
| EP | 855189 A2 | 7/1998 |
| EP | 1838110 A1 | 9/2007 |
| EP | 1639291 B1 | 5/2009 |
| EP | 2587127 A1 | 5/2013 |
| GB | 2230335 | 10/1990 |
| GB | 2267746 | 12/1993 |
| GB | 2323159 A | 9/1998 |
| GB | 2379731 A | 3/2003 |
| GB | 2385413 A | 8/2003 |
| GB | 2443926 | 5/2008 |
| GB | 2455598 A | 6/2009 |
| GB | 2527626 | 12/2015 |
| JP | H0652709 | 2/1994 |
| JP | H1057464 A | 3/1998 |
| JP | 2000284730 A | 10/2000 |
| JP | 200818075 A | 8/2008 |
| WO | WO1982002756 A1 | 8/1982 |
| WO | WO1985003561 A1 | 8/1985 |
| WO | WO1987004506 A1 | 7/1987 |
| WO | WO1996025624 A1 | 8/1996 |
| WO | WO2001092780 | 12/2001 |
| WO | WO2003011349 | 2/2003 |
| WO | WO2006020839 A2 | 2/2006 |
| WO | WO2008092753 A2 | 8/2008 |
| WO | WO2010009575 | 1/2010 |
| WO | WO2012000418 A1 | 1/2012 |
| WO | WO2012099718 A1 | 7/2012 |
| WO | WO2013020263 A2 | 2/2013 |
| WO | WO2013020439 | 2/2013 |
| WO | WO2014139483 A1 | 9/2014 |
| WO | WO 2016000517 | 1/2016 |

OTHER PUBLICATIONS

U.S. Appl. No. 15/336,553, filed Oct. 27, 2016, Li.
International Search Report and Written Opinion for PCT Application No. PCT/CN/2014/073557 dated Jul. 2, 2014.
International Search Report for PCT Application No. PCT/US2009/054401 dated Oct. 26, 2009.
EP Search Report for European Patent Application No. 12185984.7 dated Dec. 14, 2012.
Engineer's Handbook (Epoxy definition), http://engineershandbook.com/Materials/epoxy.htm, Jul. 18, 2013.
Nagashima, H. et al., "Introduction to Chaos, Physics and Mathematics of Chaotic Phenomena," Institute of Physics Publishing, 1999.
Definition of "Electromagnet" in the Encarta World English Dictionary, Aug. 1999.
Lab M3: The Physical Pendulum, Physics 1140—Experimental Physics, Course Laboratory Instructions, 2000.
Supplementary Search Report and Opinion for EP 14764844, dated Jul. 28, 2016, 12 pages.
International Search Report for PCT/CN2014/091362 dated Apr. 3, 2015, 2 pages.
UK Combined Search and Examination Report for GB1613387.8, dated Sep. 9, 2016, 10 pages.
UK Combined Search and Examination Report for GB1613393.6, dated Sep. 9, 2016, 10 pages.
Canadian Examination and Search Report for CA2936224, dated Sep. 30, 2016, 5 pages.
UK Combined Search and Examination Report for GB1613391.0, dated Sep. 19, 2016, 9 pages.
Canadian Examination and Search Report for CA2936225, dated Sep. 29, 2016, 5 pages.
German Office Action issued for German Patent Application No. 102016008225.9, dated Dec. 19, 2016.
Canadian Examination Report issued for Canadian Patent Application No. 2930099, dated Jan. 5, 2017.
Canadian Examination Report issued for Canadian Patent Application No. 2930099, dated Aug. 15, 2016.
German Office Action issued for German Patent Application No. 102016008825.7, dated Mar. 20, 2017.

* cited by examiner

100

SCENTED IMITATION CANDLE DEVICE

RELATED APPLICATIONS

This patent document claims priority to Chinese Patent Application No. 201710214532.9, filed Apr. 5, 2017. The entire contents of the before mentioned Chinese patent application is incorporated by reference in this patent document.

TECHNICAL FIELD

The subject matter of this patent document relates to a candle device that use an imitation flame, and particularly, to features that produce an aromatic scent.

BACKGROUND

Traditional true flame candles, when lit, provide a pleasant ambience in many homes, hotels, churches, businesses, etc. Traditional candles, however, provide a variety of hazards including risk of fire, damage to surfaces caused by hot wax, and the possible emission of soot. Flameless candles have become increasingly popular alternatives to traditional candles. With no open flame or hot melted wax, flameless candles provide a longer-lasting, safe, and clean alternative. Such imitation candle devices often include light sources, such as LEDs, and include electronic circuits that control the operation the imitation candle device.

Along with the development of new technologies, scented candles that are electrically powered have appeared in the market. These electronic scented candles simulate a flickering flame, which plays a great role in creating the proper atmosphere for the above venues and household environments. In addition to their use as a decorative piece, these candles can provide additional practical functions such as releasing a scent by using a fan that forces the scent to a scent outlet for release into an external environment. However, such electronic scented candles often do not produce a satisfactory scent, and are not convenient to use

SUMMARY

The disclosed technology relates to an electronic scented candle that is convenient to use and enables rapid generation and dissipation of scented material.

In one exemplary aspect, an electronic candle device is disclosed. The device includes a shell including a through hole; a flame element protruding through the through hole; an installation lid including a locking base to allow removable coupling of a fragrance container; a scent chamber including a locking clip, a first channel, a second channel, a third channel, and a fourth channel, wherein the scent chamber is removably coupled to the locking base by the locking clip; and an air pump configured to pump air, wherein the first channel of the scent chamber is removably coupled to a first section of a fragrance container to direct the pumped air into the fragrance container, wherein the second channel of the scent chamber is removably coupled to a second section of a fragrance container to draw, under air pressure of the pumped air, a fragrance material from the fragrance container into the scent chamber, wherein the third channel of the scent chamber is coupled to the air pump to allow pumped air to enter the scent chamber, and wherein the fourth channel of the scent chamber is coupled to the through hole to allow a fragrance material to reach an external environment of the electronic candle device.

In some embodiments, the device further includes the fragrance container that is removably coupled to the installation lid. In some embodiments, the device further includes a fifth channel coupled to the first channel of the scent chamber and a sixth channel coupled to the second channel of the scent chamber. In some implementations, the device further includes a suction tube coupled to the sixth channel to facilitate drawing of the fragrance material from the fragrance container to the scent chamber.

In some embodiments, the installation lid includes a mount support positioned removably on the installation lid to facilitate coupling of a fragrance container. In some embodiments, the installation lid includes a protrusion to facilitate correct alignment of the installation lid and the fragrance container.

In some embodiments, the device further includes an indicator positioned at an external surface of the electrical candle device to indicate a location of the protrusion. In some implementations, a first end of the second channel that is coupled to the scent chamber has a smaller dimension than a second end of the second channel. In some embodiments, the second channel has a tapered shape. In some embodiments, a bottom surface of the scent chamber has a funnel shape.

In some embodiments, the device further includes a central control circuit, a power supply, and one or more tilt sensors, wherein each of the one or more tilt sensors is configured to sense a tilt angle of the electronic candle device, the one or more tilt sensors further configured to transmit a signal to the central control circuit to shut down the power supply upon sensing that the tilt angle is greater than or equal to a predetermined threshold angle. In some implementations, the predetermined threshold angle is 45 degrees.

In some embodiments, the device includes a valve coupled to the fourth channel, wherein the valve is configured to, upon receiving a signal from the central control circuit indicative that the tilt angle is greater than or equal to the predetermined threshold angle, close the fourth channel to prevent the fragrance material from spilling outside of the electronic candle device. In some embodiments, the device includes a sound insulation layer around the air pump for reducing noise caused by the air pump to lower than or equal to 55 dB. In some implementations, the device includes an anti-vibration component positioned at an external side of the air pump for reducing vibration caused by the air pump.

In some embodiments, the shell includes an observation window corresponding to the fragrance container for allowing a user to observe a remaining quantity of the fragrance material in the fragrance container. In some implementations, the device includes a light source positioned within the shell, the light source configured to illuminate a fragrance container so that a remaining quantity of a fragrance material in the fragrance container can be observed via the observation window.

In some embodiments, the flame element is configured to retract into the shell when the electronic candle device is turned off. In some implementations, the device includes a dark-colored component protruding through the through hole, the dark-color part configured to have an appearance of a wick. In some embodiments, the device includes a light source positioned in proximity to the through hole, wherein the air pump is configured to pump air at a high pressure to allow the fragrance material in the fragrance container to reach the external environment in a smoke form, and wherein the light source is configured to illuminate the flame element and the fragrance material in the smoke form to create an appearance of a real flame.

The details of one or more implementations are set forth in the accompanying attachments, the drawings, and the description below. Other features will be apparent from the description and drawings, and from the claims.

DETAILED DESCRIPTION

In this patent document, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner.

Imitation candle devices can simulate a real candle with a flame that resembles a real-life flame with flickering effects using optical, mechanical and electrical components. As technologies advance, there is a demand for imitation candle devices that can provide additional functions. This patent document describes imitation candle devices that are capable of releasing pleasant scents into an external environment.

Figure 1:
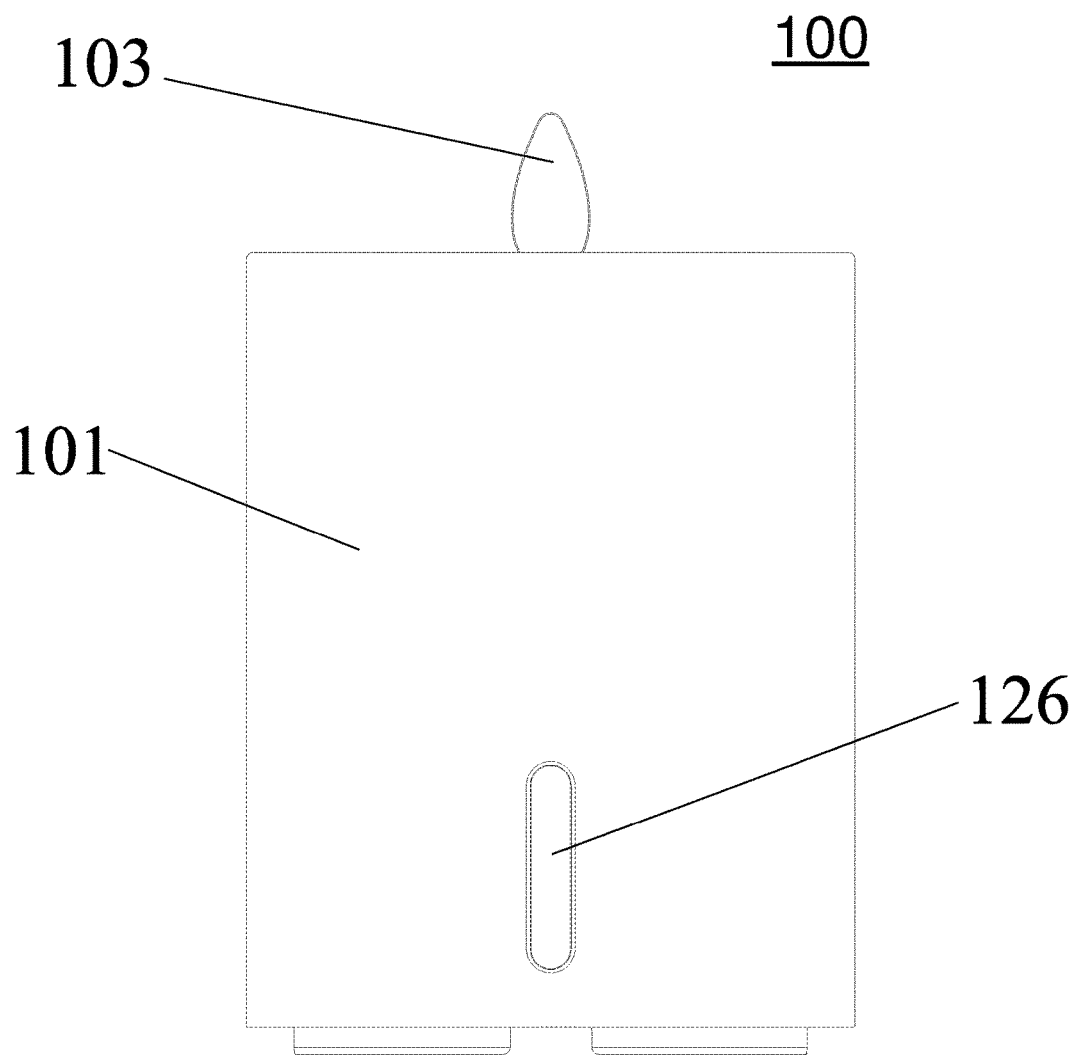
FIG. 1 shows a scent producing imitation candle device in accordance with an exemplary embodiment.

FIG. 1 illustrates an exemplary scent producing imitation candle device 100 in accordance to technology disclosed herein. The device 100 includes a flame element 103 and a shell 101. The device 100 also includes a scent-producing mechanism positioned within the shell 101 to produce scent and an observation window 126 for the user to see whether there is sufficient scent material.

Figure 2A:
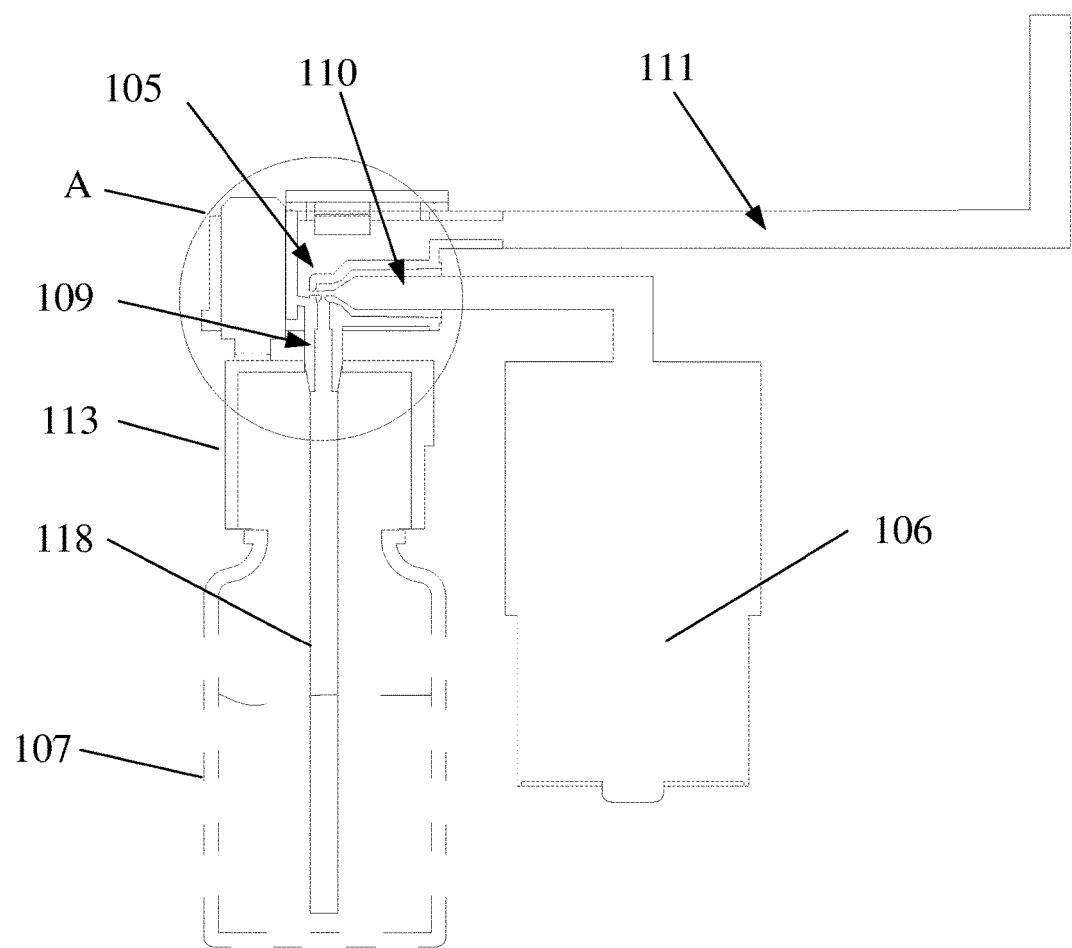
FIG. 2A shows certain components of a scent-producing mechanism within an imitation candle device including a scent chamber and an air pump in accordance with an exemplary embodiment.
Figure 2B:
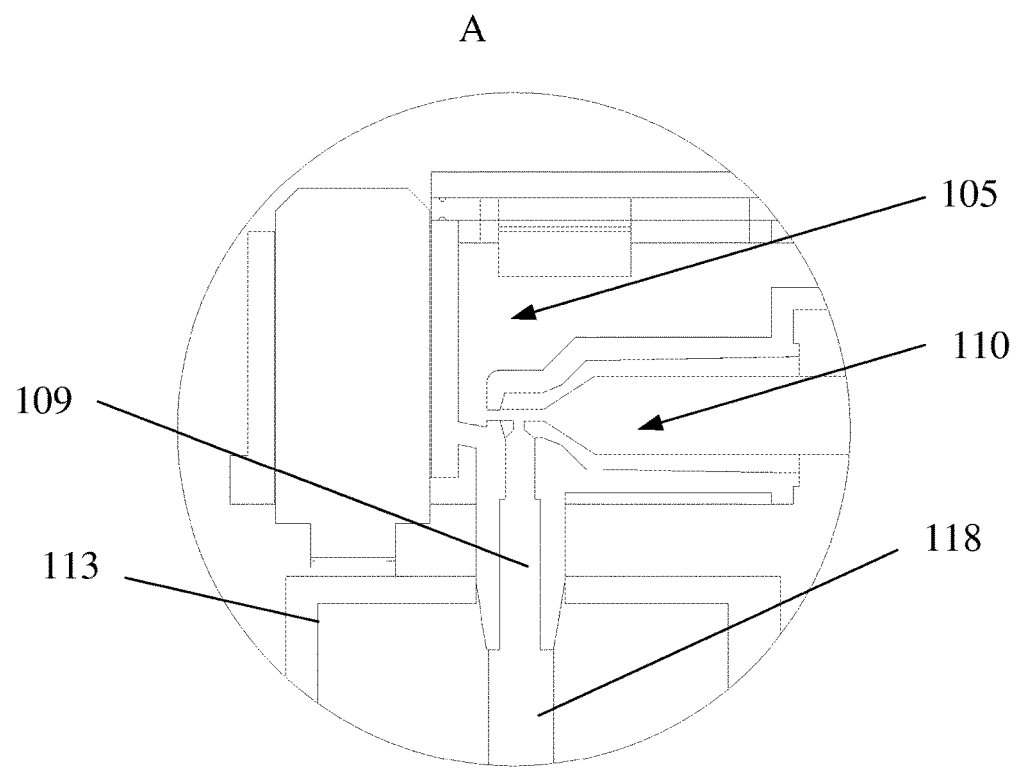
FIG. 2B shows an enlarged detailed view of some of the components illustrated in FIG. 2A.
Figure 2C:
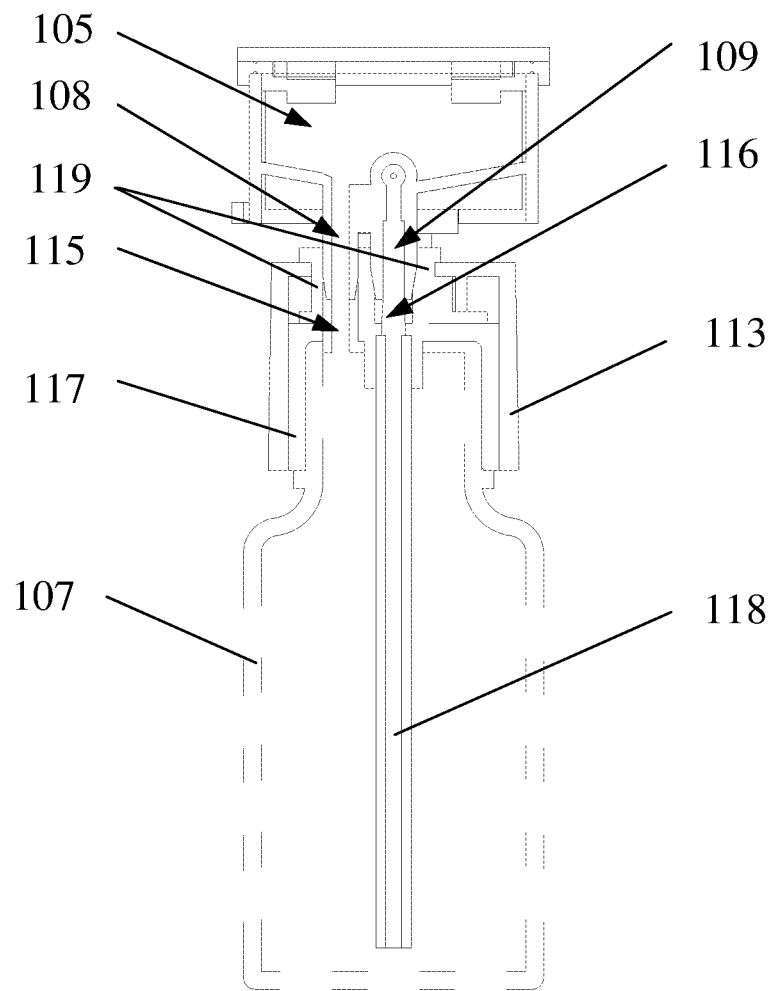
FIG. 2C shows certain components of a scent-producing mechanism within an imitation candle device including a scent chamber in accordance with an exemplary embodiment.

FIGS. 2A-2C show some exemplary components of a scent-producing mechanism within an imitation candle device 100. In some embodiments, a scent producing mechanism includes a scent chamber 105. The scent chamber 105 includes a first channel 108 (shown in FIG. 2C) and a second channel 109 (shown in FIGS. 2A-2B). The first channel 108 is coupled to (or is in communication with) the air inside a fragrance container 107, and the second channel 109 is coupled to (or in communication with) the fragrance inside the fragrance container 107. As shown in FIG. 2A, the scent chamber 105 further includes a third channel 110 and a fourth channel 111. The third channel 110 is configured to allow outside air to enter the scent chamber 105, and the fourth channel is configured to output a scent produced from the scent chamber 105 to the outside of the candle device 100. In some implementations, the third channel 110 is coupled to an air pump 106 to allow air to enter the scent chamber 105.

In some embodiments, the air pump 106 pumps air into the scent chamber 105 via the third channel 110 such that the air pressure of the scent chamber 105 keeps increasing. The air in the scent chamber 105 enters the fragrance container 107 via the first channel 108 under high air pressure such that the air pressure in the fragrance container 107 keeps increasing as well. The fragrance in the fragrance container 107 is then transported under pressure into the scent chamber 105 via the second channel 109. The high pressure produced by the air pump 106 allows the fragrance to be fully atomized. Because the air pressure in the scent chamber 105 is higher than the air pressure of the external environment, the atomized fragrance leaves the scent chamber 105 via the fourth channel 111 dissipated outside of the candle device, thereby releasing a scent. In some embodiments, instead of having the air pump 106, a fan may be used to supply the air to the third channel 110, and the fan produces an air flow with a velocity that is directed into the scent chamber 105.

The air pump provides several advantageous aspects as compared to a fan. First, the air pump 106 can effectively drive a fragrance to the second channel 109 inside the electronic candle 100 by producing a high air pressure. Meanwhile, the high air pressure can fully atomize a liquid fragrance, which improves the aromatic effect of the fragrance. Second, the atomized fragrance is more concentrated as compared to fragrance dispersed using other mechanisms, e.g., a fan. Furthermore, the air pressure produced by the air pump 106 is adjustable, thereby allowing the user to adjust the atomization rate of the fragrance. For example, when a fan is used to drive air flow to disperse the liquid fragrance, the magnitude and direction of its pressure on the fragrance may not be precisely controlled even though the wind speed and direction of the fan can be adjusted. The air pump, on the other hand, can apply air pressure of different magnitudes and directions in a relatively precise manner, thereby achieving more effective control by the user.

In some embodiments, an installation lid 113 can be used to connect the fragrance container 107 to the scent chamber 105. In some implementations, the installation lid 113 includes a fifth channel 115 and a sixth channel 116 (shown in FIG. 2C), which are coupled to the first channel 108 and the second channel 109 of the scent chamber 105, respectively. In some embodiments, the installation lid 113 includes a mount support 117 for mounting the fragrance container 107 in the installation lid 113. The mount support 117 is positioned on the installation lid 113 in a removable manner to facilitate easy disassembling of the mount support 117 from the installation lid 113 when the mount support 117 needs to be cleaned. The removable connection mechanism includes, but is not limited to, a snap connection. In some embodiments, the installation lid 113 further comprises a suction tube 118 disposed inside of the mount support 117. The suction tube 118 may extend into the mount support 117 and may be coupled to the sixth channel 116 to guide the fragrance in the fragrance container 107 to rise into the scent chamber 105 via the suction tube 118. In some embodiments, the suction tube 118 is fixed to the mount support 117 through an interference fit between the end of the suction tube 118 and the mount support 117. In some embodiments, the mount support 117 includes a gasket that may be made of rubber or silica gel, such that an excellent seal can be achieved when the fragrance container 107 is mounted onto the mount support 117. In some implementations, an elastic element 119 is further disposed between the installation lid 113 and the mount support 117. The elastic element 119 can be used to improve the tightness between the installation lid 113 and the installation. The elastic material 119 can also reduce vibration of the installation lid 113 and/or the mount support 117, thereby reducing noise. The elastic material 119 may be rubber or silica gel. In some embodiments, the inner side of the mount support 117 is of a cylindrical structure and comprises threads to facilitate the fixation of the fragrance container 107 onto the mount support 117. In some implementations, the fragrance container 107 has its own threads. The threads of the mount support 117 allow the use of various types of fragrance containers 107 so long as they have compatible threads, thereby improving the universality of the scent producing device. In some embodiments, the fragrance container 107 may also be fixed through a snap connection. In some implementations, moreover, the threads of the mount support 117 are generally used and therefore can fit most perfume bottles on the market, which also improves the universality of the scent producing device (i.e. a variety of general fragrance containers are compatible with the candle device).

Figure 7A:
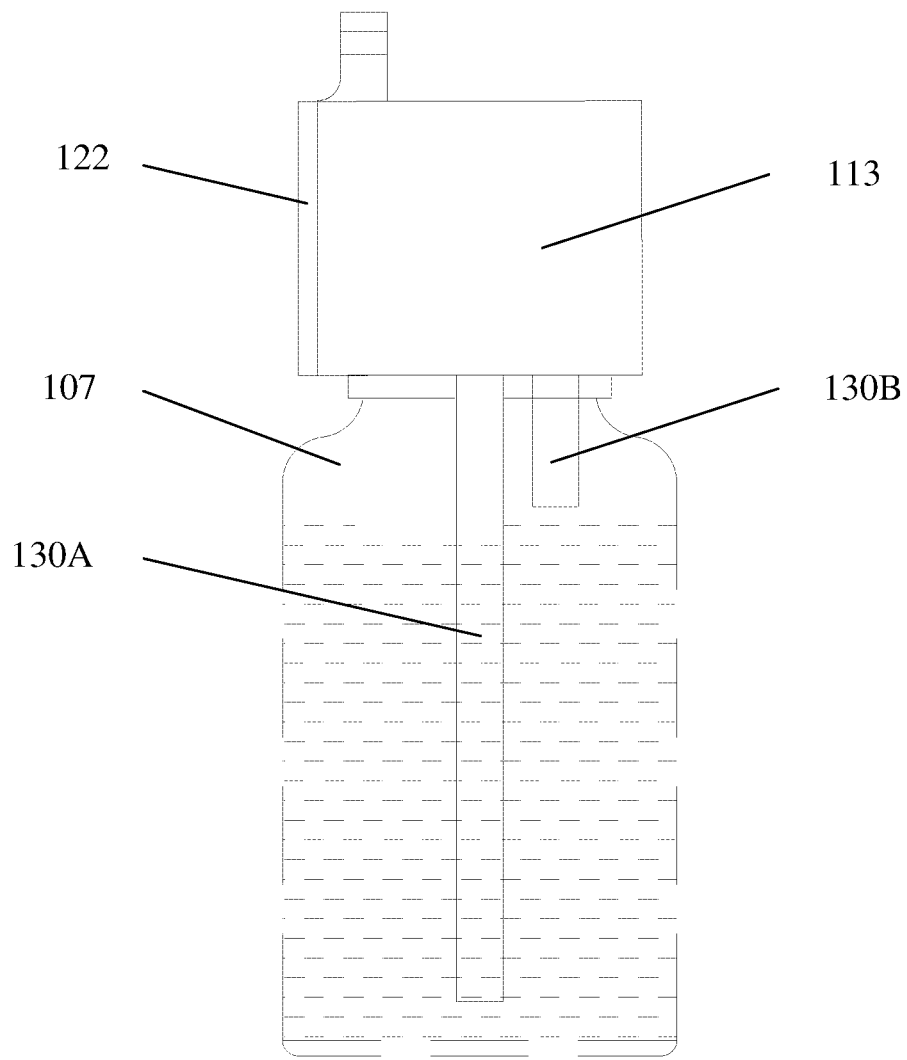
FIG. 7A shows an installation lid and connection pipes of an imitation candle device in accordance with an exemplary embodiment.
Figure 7B:
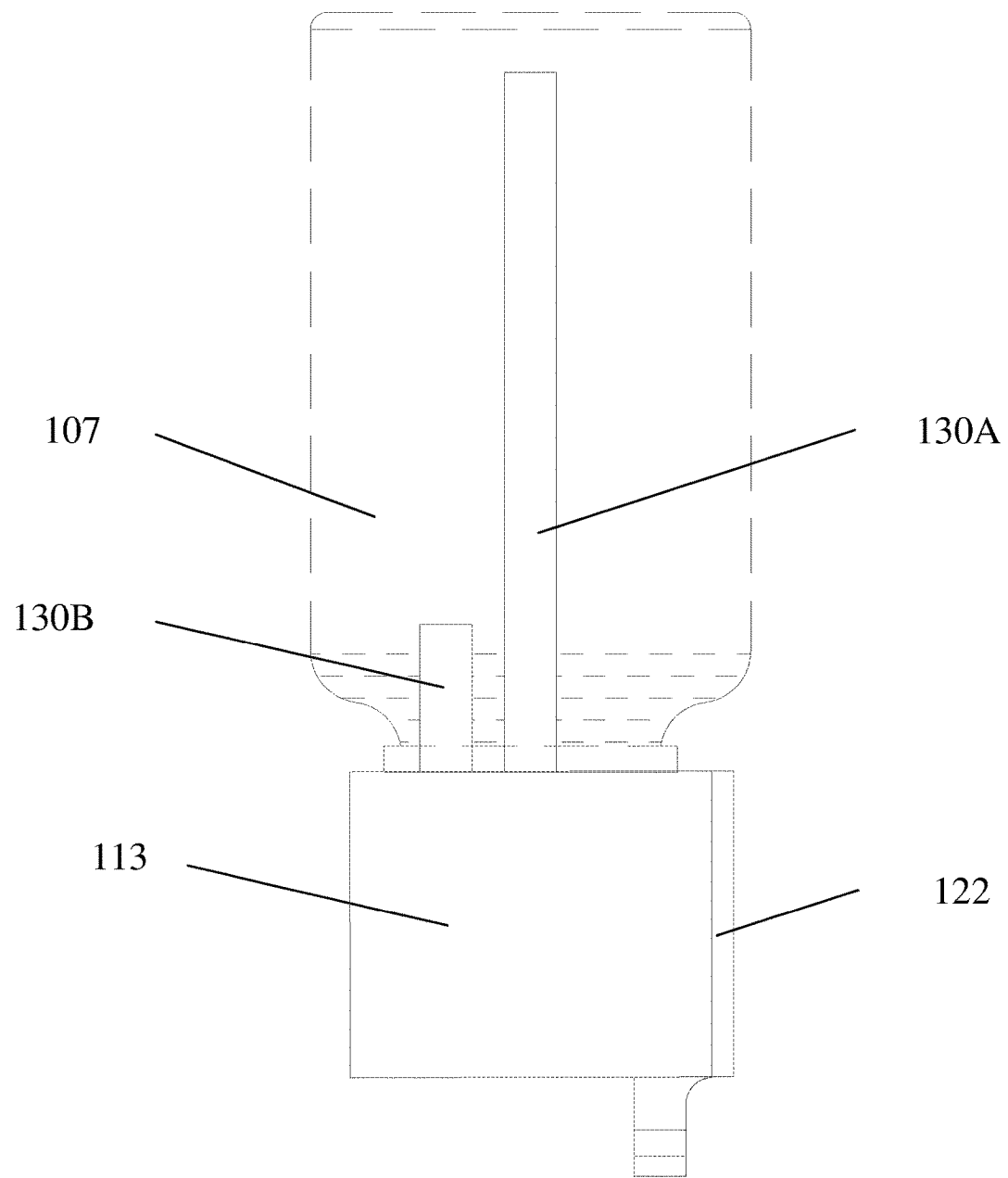
FIG. 7B shows an inverted installation lid and connection pipes of an imitation candle device in accordance with an exemplary embodiment.

In some embodiments, such as shown in FIGS. 7A-B, the first channel is coupled to an air portion inside the fragrance container 107 via the connection pipe 130B (shown in FIG. 7B). In some implementations, the opening end of the connection pipe 130B is above the surface of the fragrance in the fragrance container 107, and the second channel extends into a fragrance portion inside the fragrance container 107 via the connection pipe 130A (shown in FIG. 7A). Usually, there is a small amount of the fragrance remaining at the bottom of the fragrance container 107 when the scent producing mechanism cannot produce scent because the fragrance is substantially consumed. When the fragrance container 107 is replaced by the user, the electronic candle 100 may be inverted so that the installation lid 113 and the fragrance container 107 can be disengaged together, as shown in FIG. 7B. The remaining fragrance in the fragrance container 107 then gathers at the opening of the fragrance container 107. Because the first channel 108 and the second channel 109 are coupled with the connection pipes 130A and 130B, whose openings are both higher than the opening of the fragrance container 107, the perfume will not flow out via the first channel or the second channel.

Figure 7C:
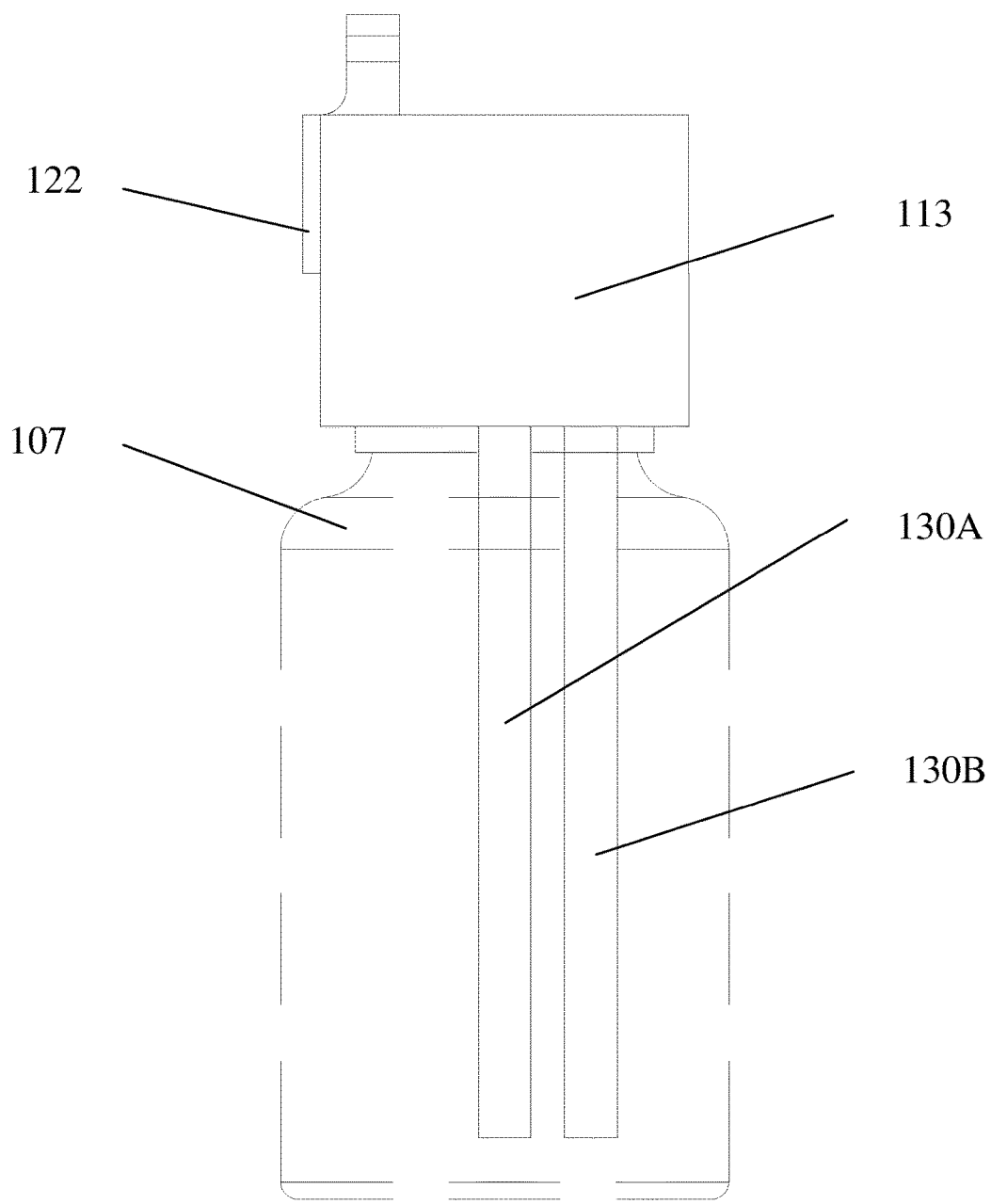
FIG. 7C shows another installation lid and connection pipes of an imitation candle device in accordance with an exemplary embodiment.

In some implementations, the first channel and the second channel are coupled to a fragrance portion inside the fragrance container 107, as shown in FIG. 7C. The first channel and the second channel extend into a fragrance portion inside the fragrance container 107 via the connection pipe 130A and the connection pipe 130B. Usually there is a small amount of the fragrance remaining at the bottom of the fragrance container 107 when the scent producing device cannot produce a scent because the fragrance is substantially consumed. When the fragrance container 107 is replaced by the user, the electronic candle may be inverted so that the installation lid 113 and the fragrance container 107 can be disengaged together. The fragrance in the fragrance container 107 then gathers at the opening of the fragrance container 107. Because the first channel and the second channel are connected with the connection pipe 130A and the connection pipe 130B, whose openings are both higher than the opening of the fragrance container 107, the perfume will not flow out via the first channel or the second channel. Meanwhile, as shown in FIG. 7C, the connection pipe 130A and the connection pipe 130B extend to the bottom of the fragrance container 107. When the fragrance container 107 is inclined or inverted, the air inside of the fragrance container 107 moves to the bottom ends of the connection pipe 130A and the connection pipe 130B, which can effectively prevent the fragrance from flowing out of the first channel and the second channel in a large quantity.

It is noted that the length of the connection pipe 130B may be set according to specific requirements, and any connection pipe 130B higher than the bottle mouth of the fragrance container 107 shall be encompassed by the present document.

Figure 4:
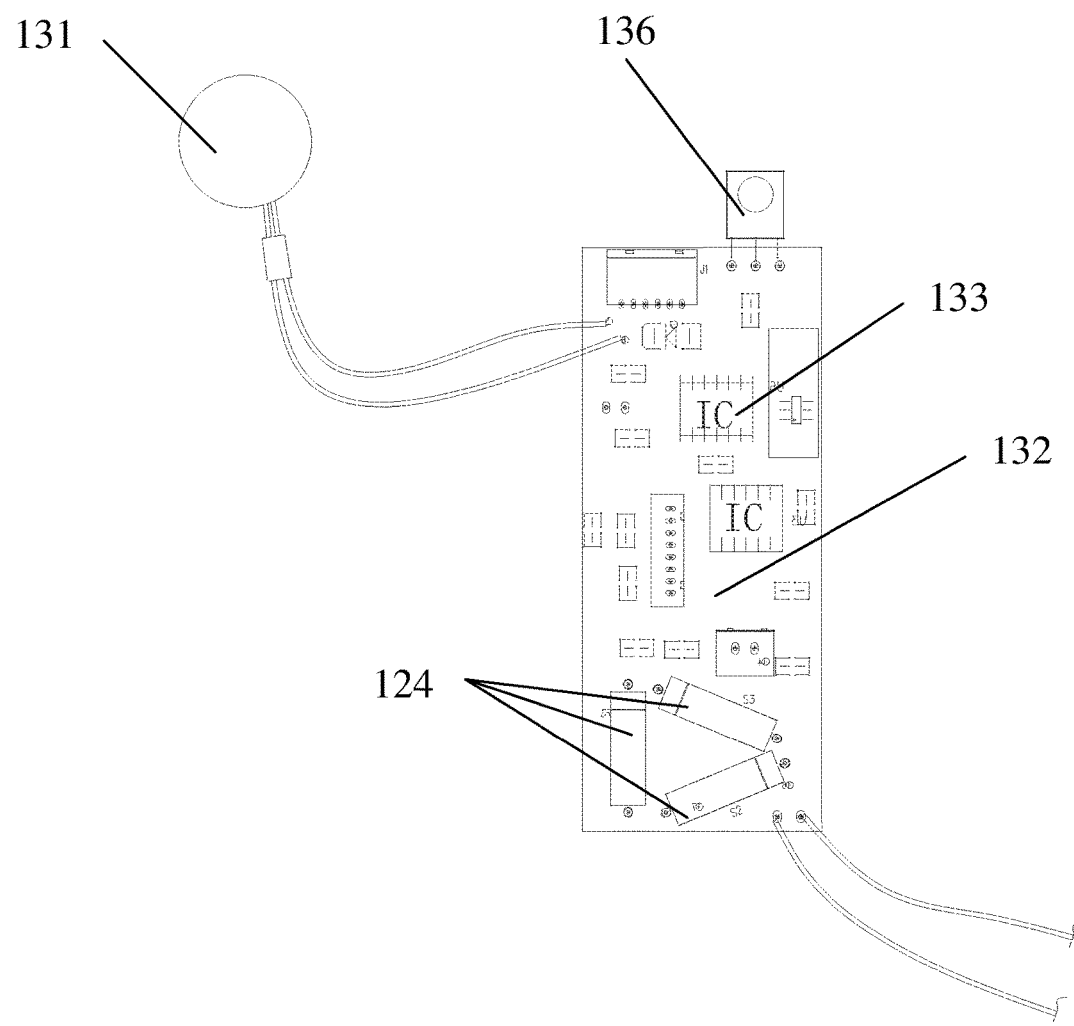
FIG. 4 shows a central control circuit board of an imitation candle device in accordance with an exemplary embodiment.

Referring back to FIGS. 2A-2B, in some embodiments, the dimension of one end of the third channel 110 that is further away from the air pump 106 can be smaller than the dimension of the remaining portion. The shape of the third channel 110 includes, but is not limited to, an evenly tapered cone, or a tapered extension in a cylindrical manner from the opening, such that the air flow in the air pump 106 has a further increased velocity when it flows out of the opening into the scent chamber along the third channel 110. The high-speed air flow output from the third channel 110 allows the fragrance to be atomized and distributed more evenly. In some embodiments, the air pump 106 can continuously pump at a rate desired by a user. In some implementations, if a user wants the produced scent to be lighter, the scent producing mechanism may be set to spray the fragrance intermittently. For example, the device may spray for five minutes (or another time duration) at every half an hour/one hour/two hour intervals. In some embodiments, a user may set the time duration, turn-on time, and turn-off time of spraying. In some embodiments, the air pump 106 is controlled via a control circuitry (such as shown in FIG. 4), e.g., through a hardware circuit such as a PCB board. In some embodiments, a control program for the air pump 106 may be written into a memory, and the control program can be executed by a processor to control operations of the air pump 106. In some embodiments, the air flow rate by the air pump 106 into the scent chamber 105 is greater than or equal to 1.0 L/min. In some implementations, the air flow rate is greater than 1.2 L/min. The velocity of the air produced by the air pump 106 can be properly controlled to allow the liquid fragrance to be fully atomized while, at the same time, preventing the fragrance to be sprayed too far, such as directly onto the wall of the scent chamber 105.

Figure 6A:
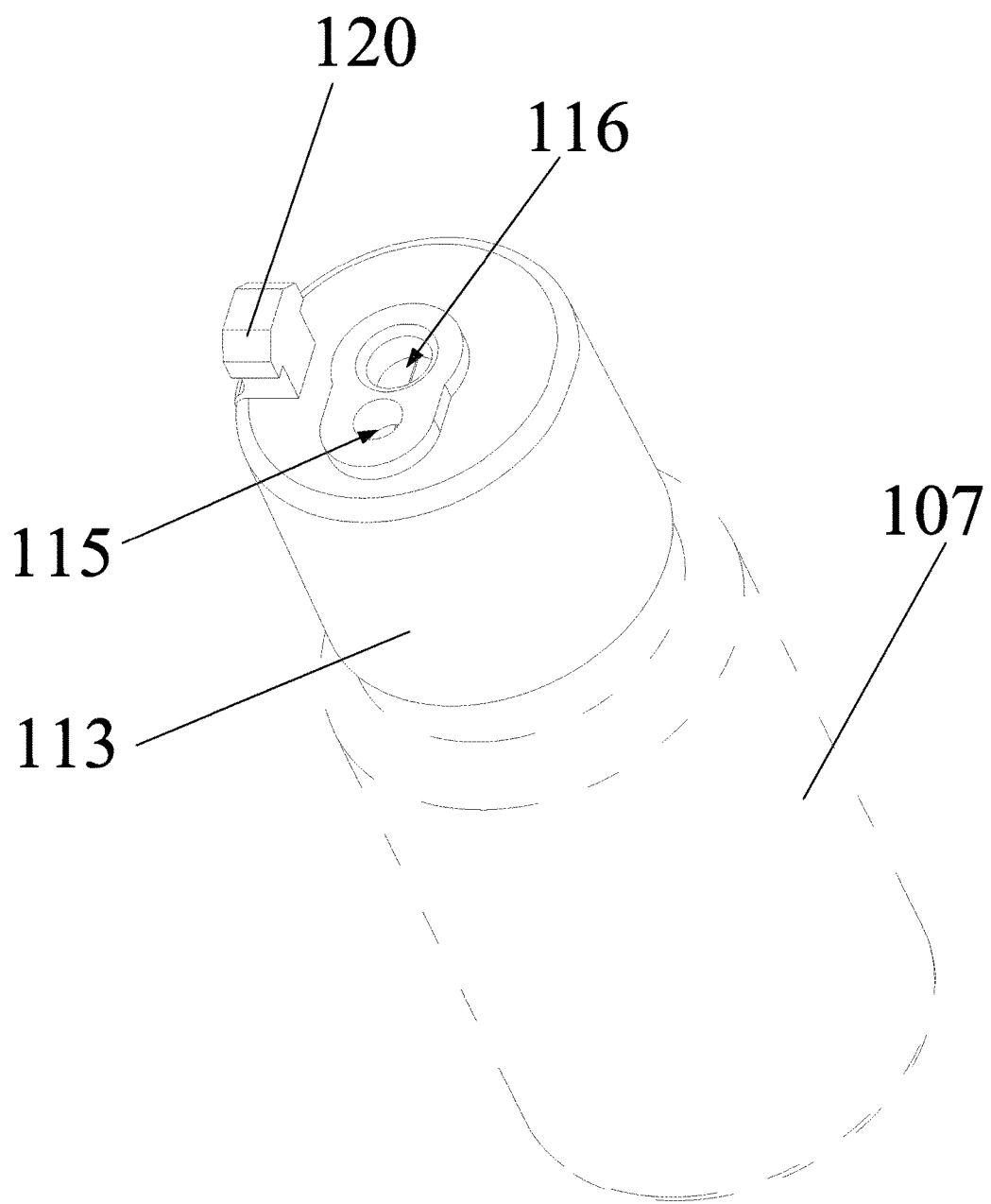
FIG. 6A shows an installation lid of an imitation candle device in accordance with an exemplary embodiment.
Figure 6B:
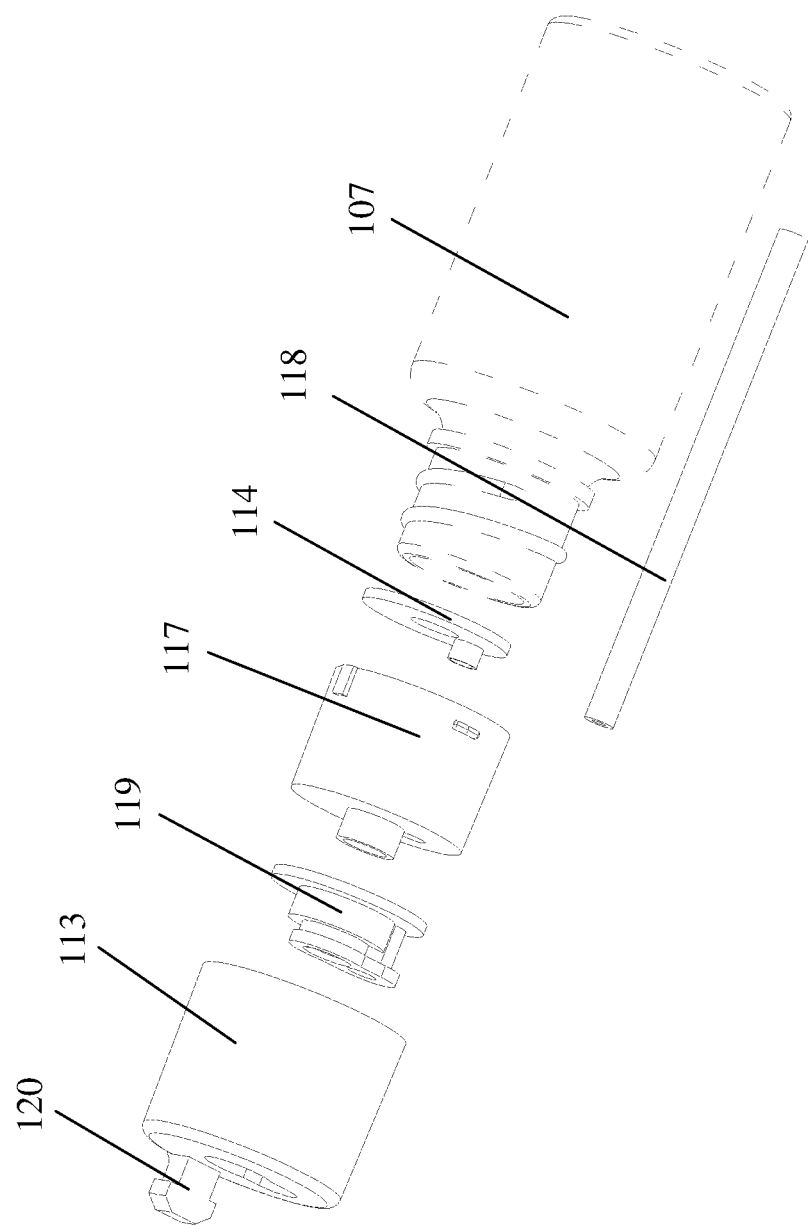
FIG. 6B shows an exploded view of components of an installation lid in accordance with an exemplary embodiment.
Figure 8A:
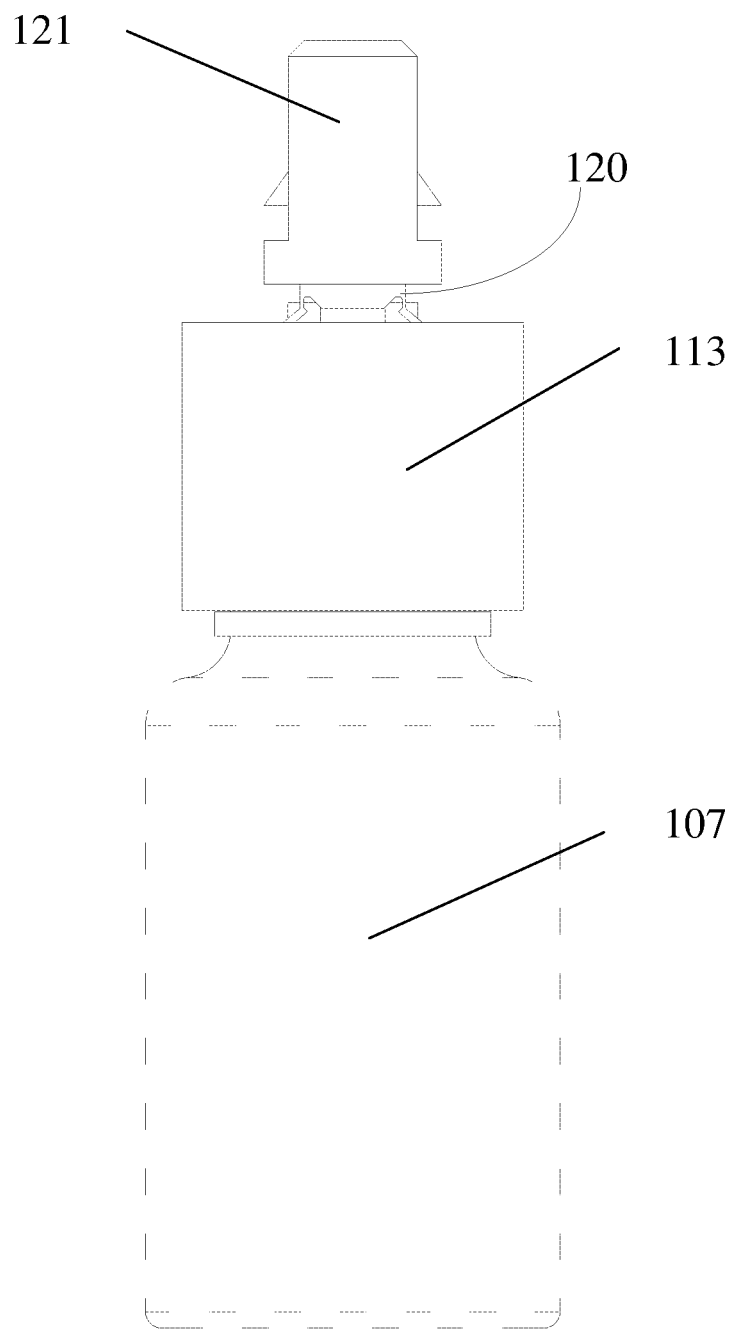
FIG. 8A shows a locking clip and a locking base of an installation lid in accordance with an exemplary embodiment.
Figure 8B:
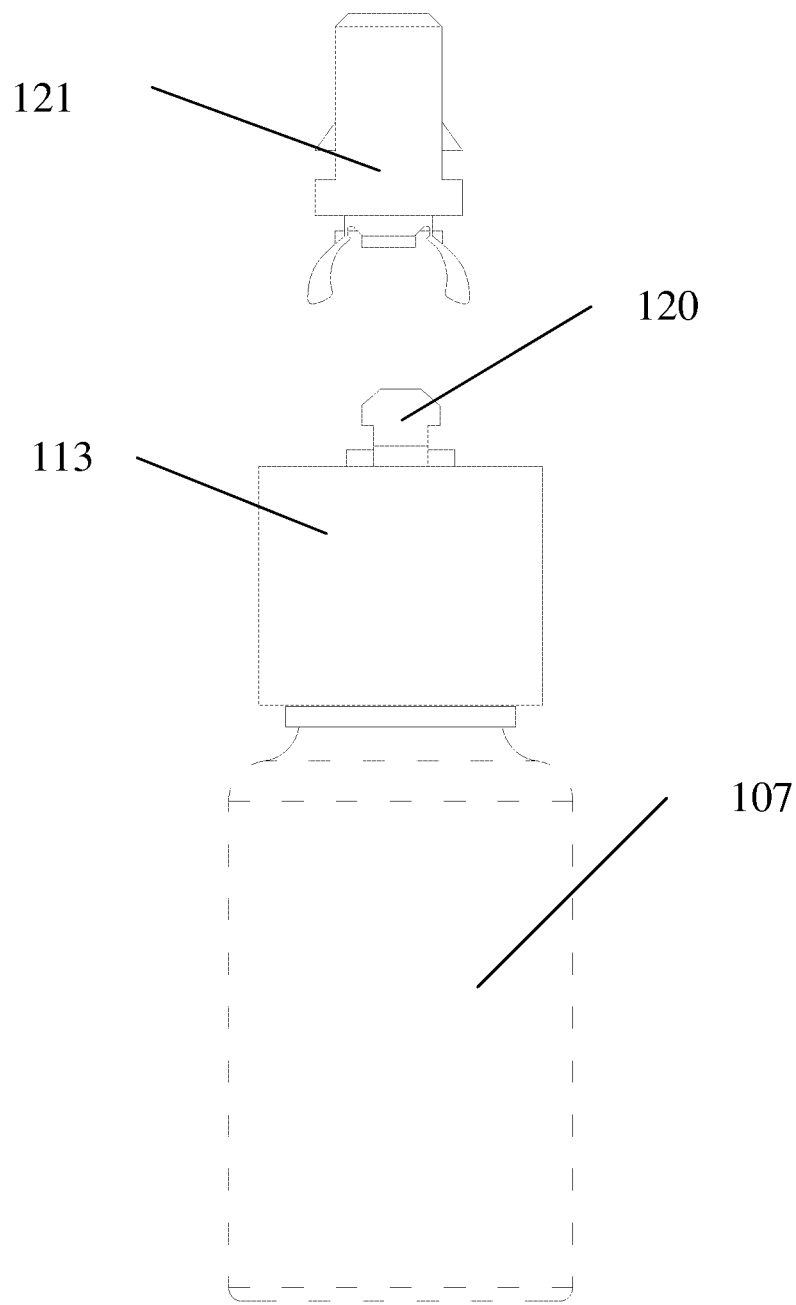
FIG. 8B shows another locking clip and another locking base of an installation lid in accordance with an exemplary embodiment.

Referring to FIGS. 8A-B, the installation lid 113 is provided with a locking clip 121, such as a lock switch, with a corresponding locking base 120 (see also FIGS. 6A-B). The locking base 120 and the locking clip 121 may be disposed on the top or one side of the installation lid 113. As shown in FIGS. 8A-B, the locking clip 121 can form a snap connection with the locking base 120. In some embodiments, the locking clip 121 is fixed on the scent chamber 105 to form an integral part with the scent chamber 105. In some embodiments, the locking base 120 has a structure that is wide at the top and narrow at the bottom, similar to a T-shaped structure.

Figure 11A:
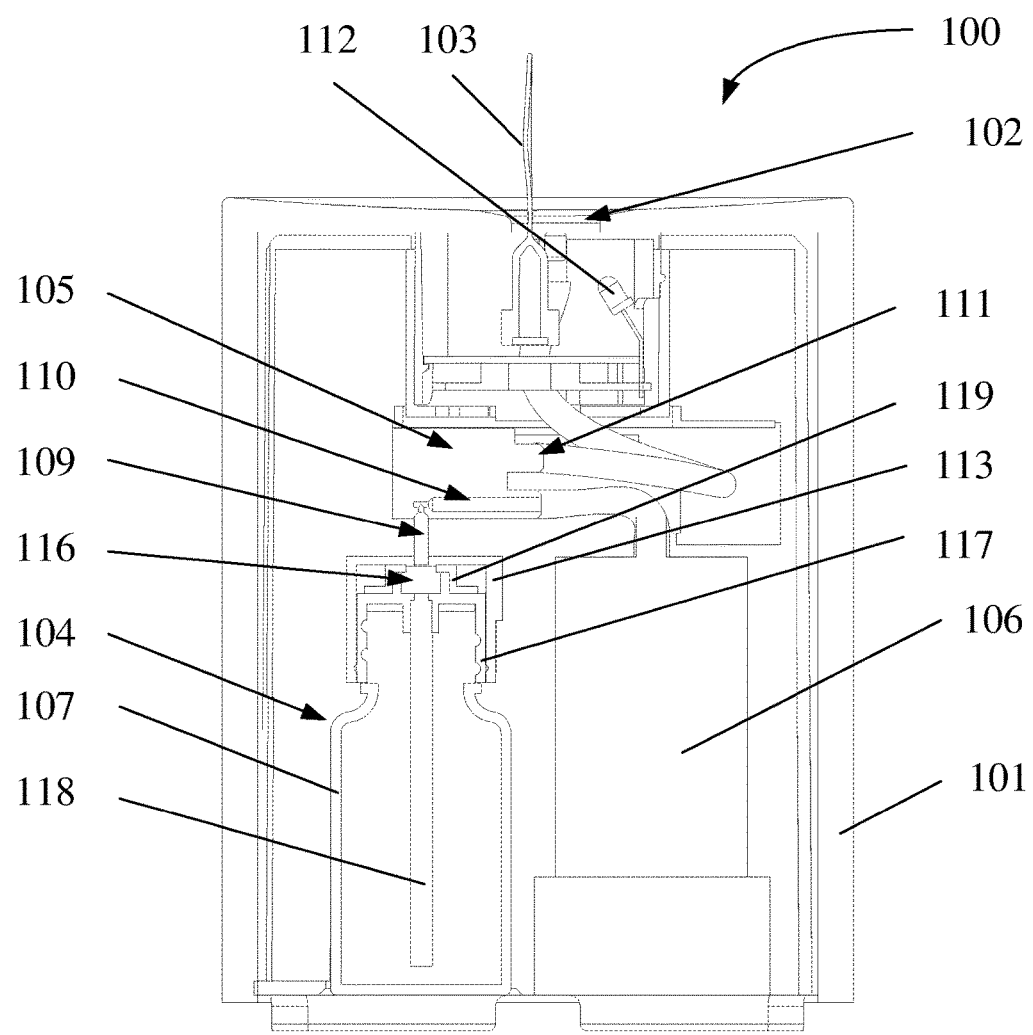
FIG. 11A shows certain components of an exemplary electronic imitation candle in accordance with an exemplary embodiment.

Referring to FIG. 11A, in some embodiments, an installation lid 113 is placed onto the fragrance container 107. The installation lid 113 along with the fragrance container 107 may, for example, be pushed into an accommodating chamber 104 from the bottom of the electronic candle 100 and snapped into the locking clip 121. If a user wants to take out the fragrance container 107, the bottom of the fragrance container 107 may be pressed, then the installation lid 113 along with the fragrance container 107 are disengaged from the locking clip 121, allowing convenient use. In some embodiments, the installation lid 113 may be placed onto the fragrance container 107 using other means. For example, it may be snapped into the locking clip 121 via the locking base 120. When the fragrance container 107 needs to be replaced, the fragrance container 107 may be rotated by an angle such that the installation lid 113 along with the fragrance container 107 are disengaged from the locking clip 121. In some embodiments, as shown in FIGS. 7A-C, a limit protrusion 122 is formed on a side of the installation lid 113, such that the installation lid 113 is installed at a fixed angle when being placed into the accommodating chamber 104, thereby making the installation easier.

It is noted that the locking mechanism is not limited to the snap connection or the lock switch as described above. It is also noted that the installation lid 113 and the fragrance container 100 may be installed upward from the bottom.

In some embodiments, the top of the installation lid 113 includes a protective layer for covering the fifth channel 115 and the sixth channel 116 (such as shown in FIG. 2C). The protective layer can be made of silica gel, rubber, or PVC film with a thickness in the range of 0.1-3.5 mm. The protective layer is mainly used to prevent the fragrance from flowing out of the fragrance container 107 when the fragrance container 107 is installed for the first time. When the fragrance container 107 is installed for the first time, a user needs to unscrew the lid of the fragrance container 107, and at the same time, screw on the installation lid 113 installed with the mount support 117 onto the fragrance container 107 in order to replace the original lid of the fragrance container 107. One way of installation is to vertically place the fragrance container 107 with its opening facing upwardly, and then align the accommodating chamber 104 of the electronic candle 100 with the fragrance container 107. However, sometimes it is relatively difficult to align the accommodating chamber 104 with the fragrance container 107.

Figure 14A:
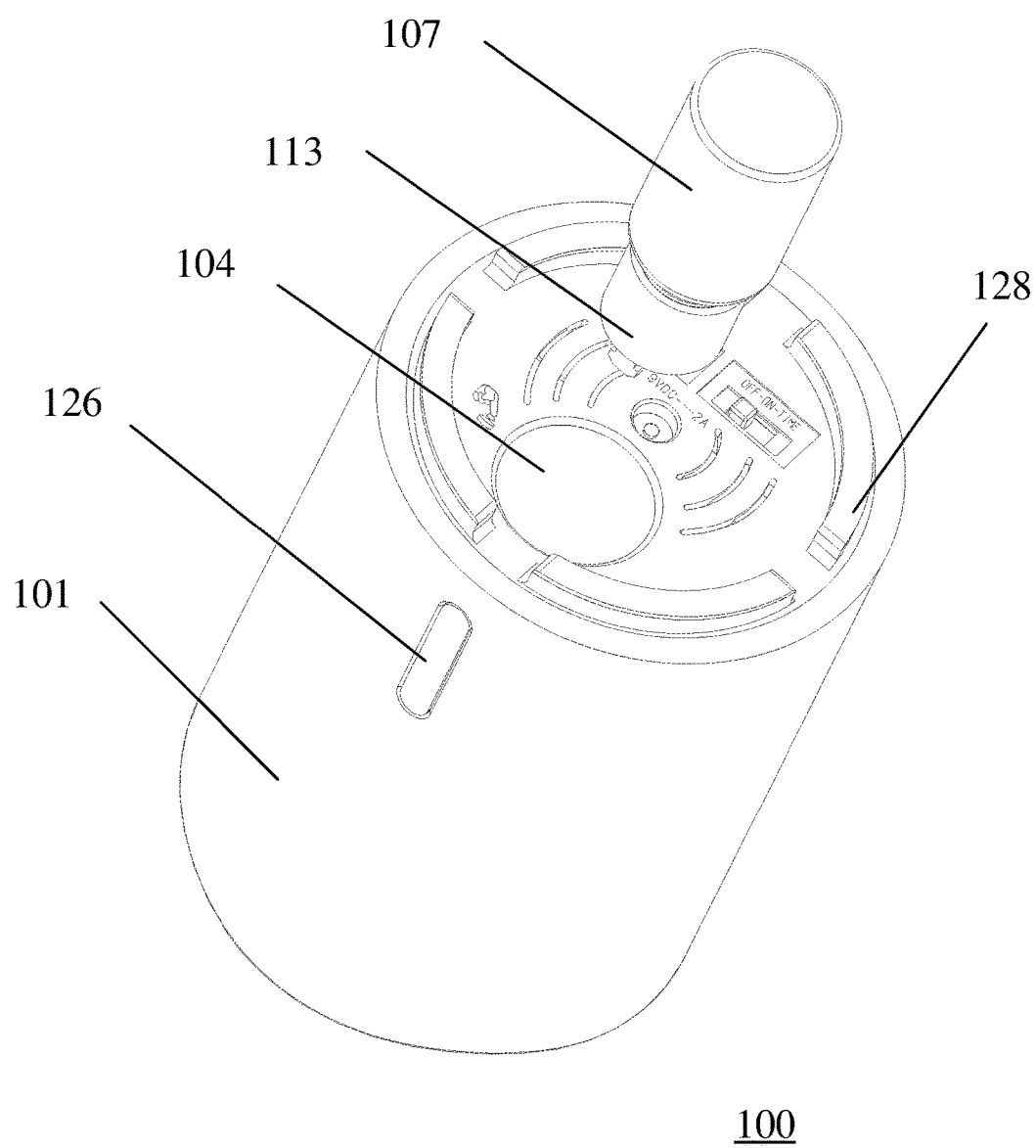
FIG. 14A shows a first step of installing a fragrance container in an imitation candle device in accordance with an exemplary embodiment.
Figure 14B:
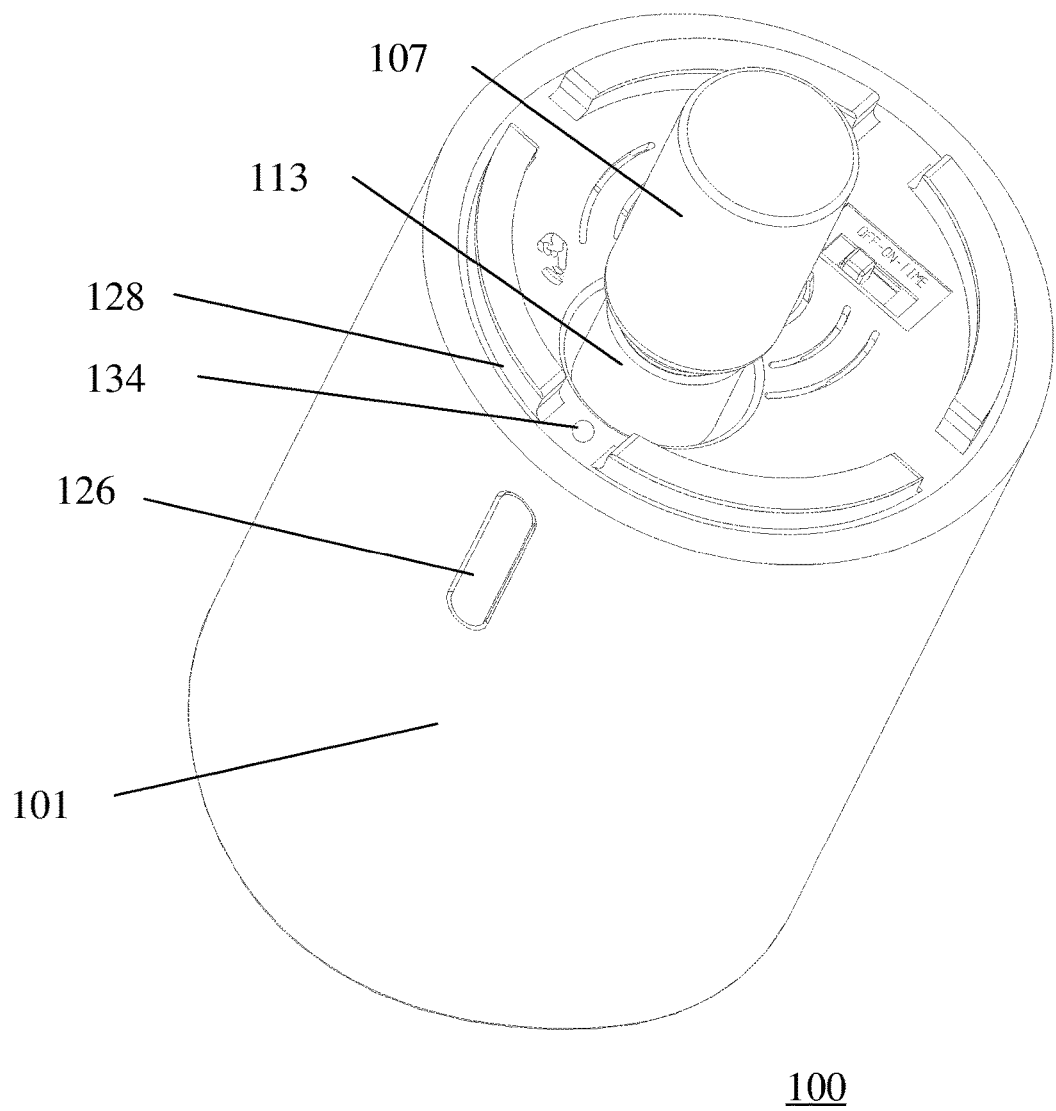
FIG. 14B shows a second step of installing a fragrance container in an imitation candle device in accordance with an exemplary embodiment.
Figure 14C:
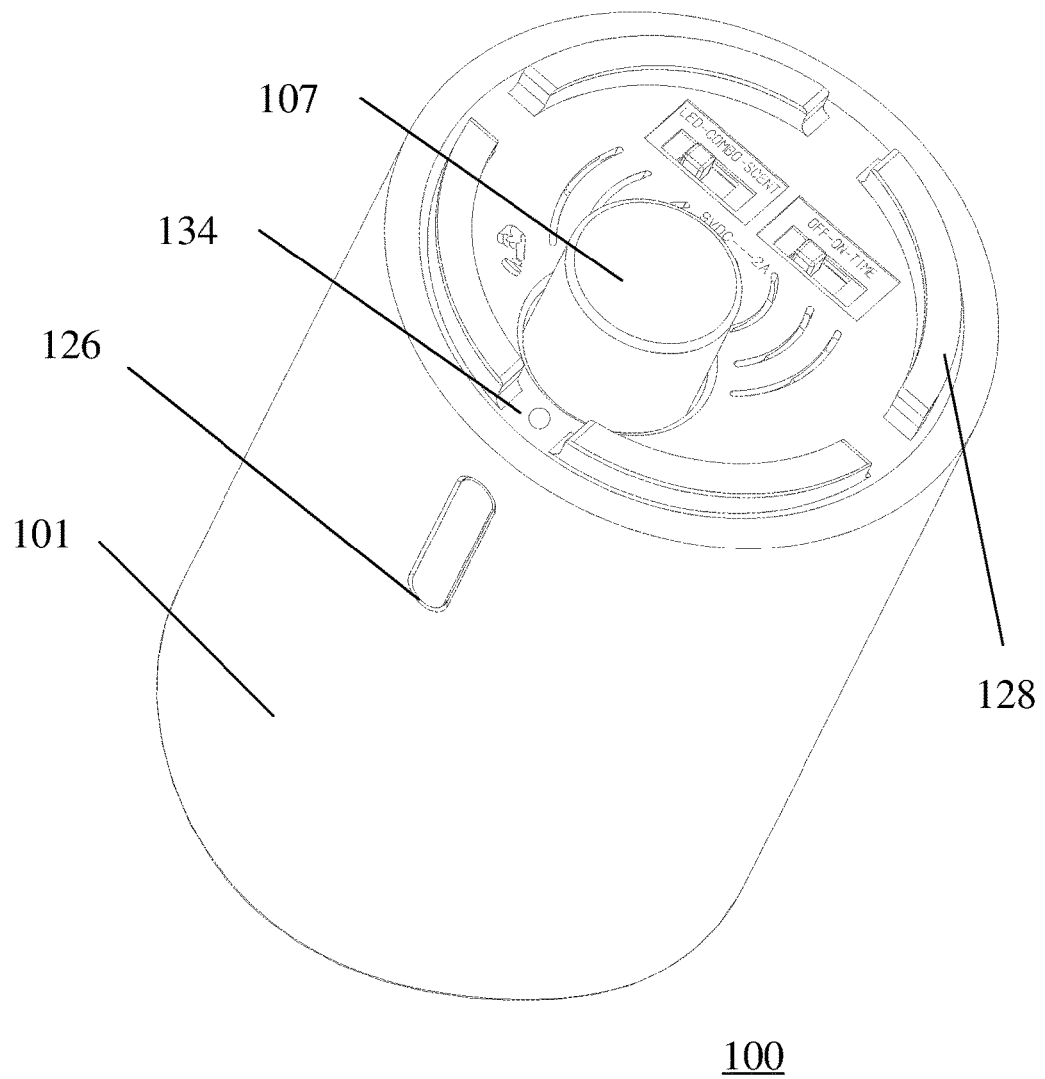
FIG. 14C shows a third step of installing a fragrance container in an imitation candle device in accordance with an exemplary embodiment.
Figure 14D:
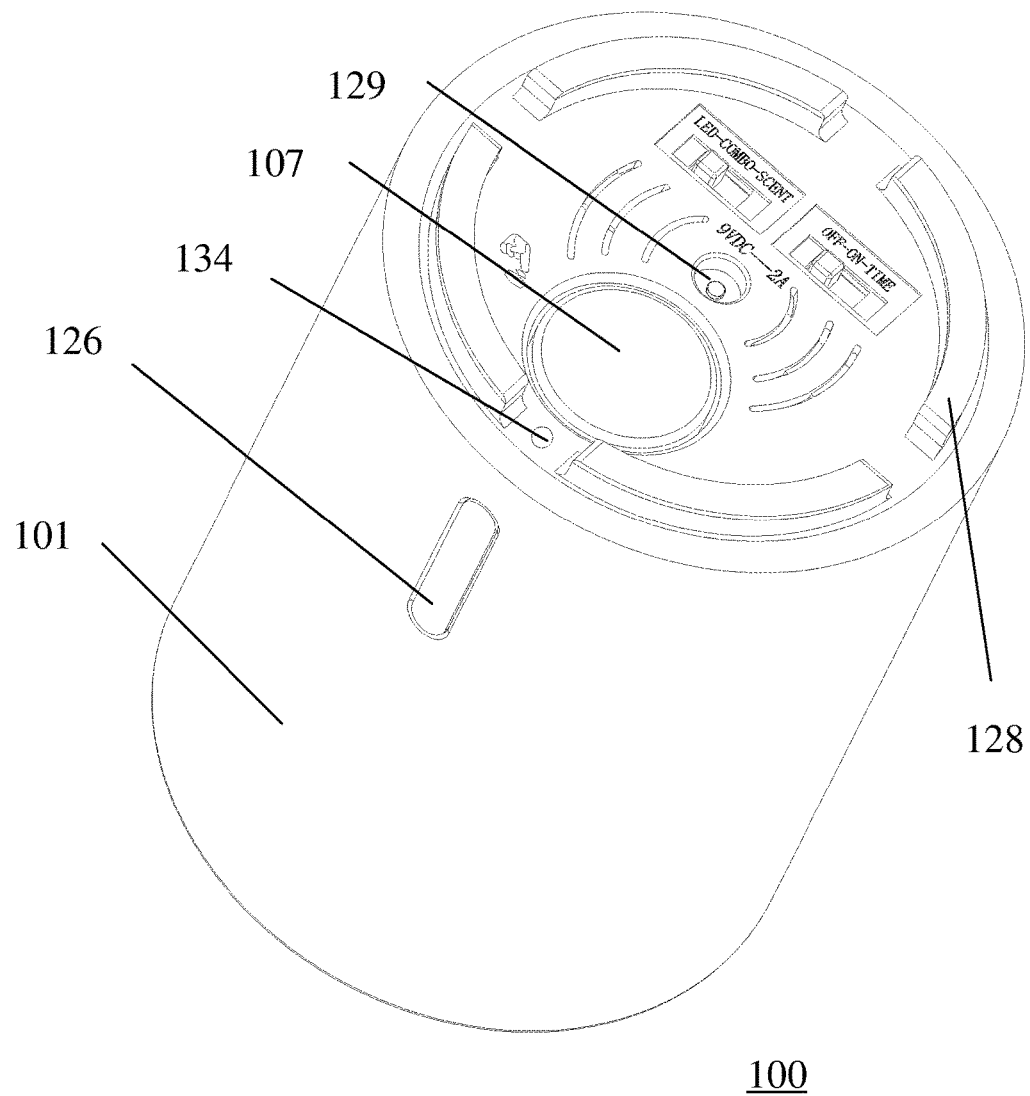
FIG. 14D shows an installed fragrance container in an imitation candle device in accordance with an exemplary embodiment.

Alternatively, the electronic candle device 100 can be inverted for the installation. As shown in FIGS. 14A-14D, the electronic candle device 100 is inverted first, and the fragrance container 107 with the installation lid 113 (such as shown in FIGS. 7A-B) is also inclined or inverted. Because the installation lid 113 includes a limit protrusion 122 (such as shown in FIGS. 7A-B), the fragrance container 107 can be installed into the electronic candle 100 only when the limit protrusion 122 is aligned with the corresponding limit groove. The protrusion 122 of the installation lid 113 enables the fragrance container 107 to be smoothly and precisely installed into the electronic candle 100, thereby preventing incorrect installation by the user. In addition, such as shown in FIGS. 14C-D, a prompt point or indicator 134 can be positioned on the bottom of the electronic candle 100 for prompting a user to align the limit projection 122 at the prompt indicator 134. The prompt indicator 134 further enables the user to install the fragrance container 107 easily and precisely. In some embodiments, the protective layer included in the top of the installation lid 113 prevents the fragrance from leaking through the suction tube 118, the fifth channel 115, and/or the sixth channel 116 on the fragrance container 107. When the fragrance container 107 is almost installed, the protective layer will be in contact with the first channel 108 and/or the second channel 109. The first channel 108 and/or the second channel 109 may push through and penetrate the protective layer, allowing the perfume to flow out. After the fragrance container 107 is installed, consequently, the first channel 108 is now coupled to the fifth channel 115, and the second channel 109 is also coupled to the sixth channel 116. This way, leakage of the fragrance container during installation can be avoided, and normal use of the fragrance container is not affected.

Furthermore, as shown in FIGS. 14A-D, the bottom of the fragrance container 107 is exposed to the outside of the electronic candle 100. Because the fragrance container 107 is typically made of a transparent material, a user can observe the remaining quantity of the perfume inside the fragrance container 107 from the bottom of the fragrance container 107.

In some embodiments, any one of the first channel 108, the second channel 109, the third channel 110, the fourth channel, the fifth channel 115, and/or the sixth channel 116 described above may be made of a hard tube, a soft tube, or an elastic material 119. In some embodiments, the first channel 108 and/or the second channel 109 may be positioned on the scent chamber 105. In some implementations, they are formed as an integral part of the scent chamber 105. The third channel 110 and/or the fourth channel may be a soft tube or a hard tube, and the specific material may be plastic, rubber, or PVC. In some embodiments, the third channel 110 and the fourth channel are fixedly disposed on the scent chamber 105. They are connected to the air pump 106 and a scent-releasing opening respectively via soft tubes. The third channel 110 and/or the fourth channel may also be formed as an integral part of the scent chamber 105. In some implementations, the fifth channel 115 and the sixth channel 116 are fixedly disposed on the installation lid 113. In some implementations, the fifth channel 115 and the sixth channel 116 may be formed as an integral part of the installation lid 113. They can be made of an elastic material 119, such as rubber or silica gel.

Figure 5A:
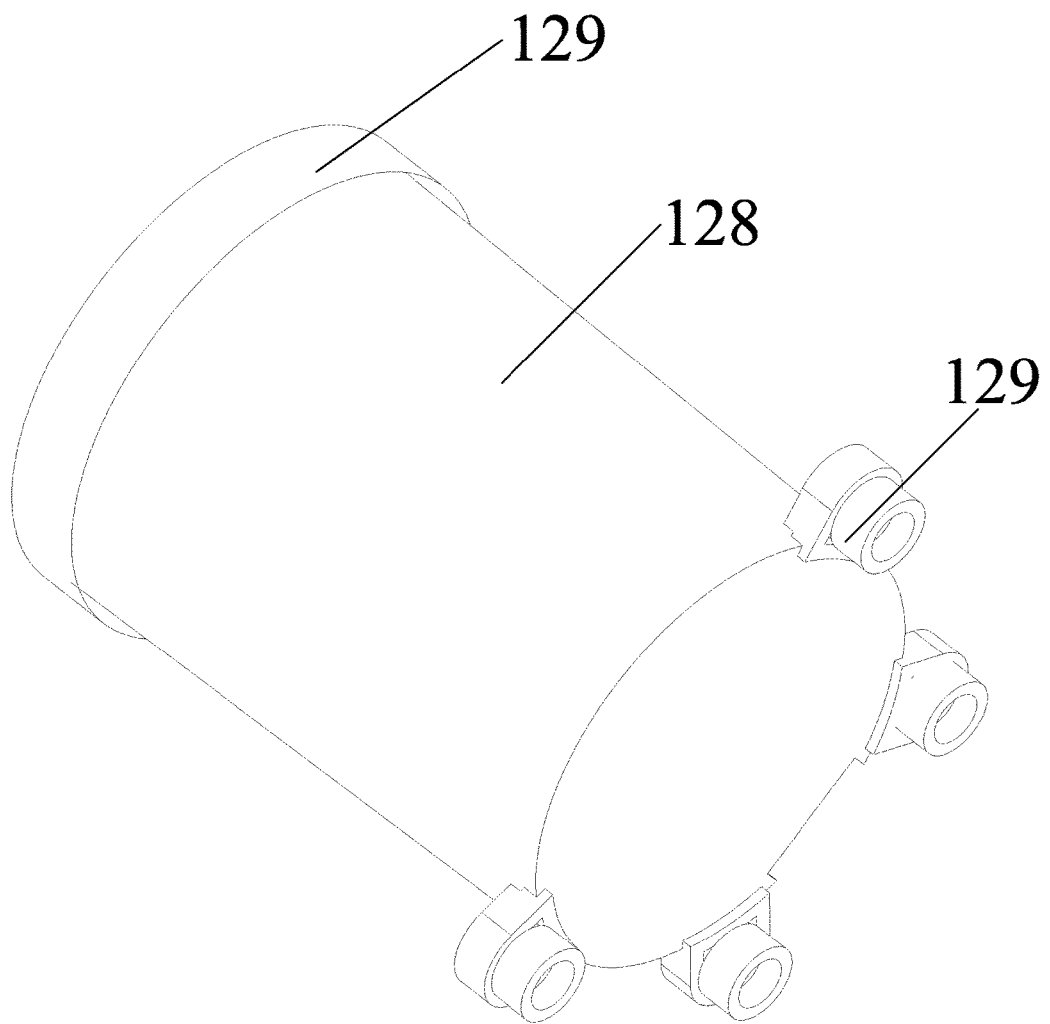
FIG. 5A shows an external side of an air pump in an imitation candle device in accordance with an exemplary embodiment.
Figure 5B:
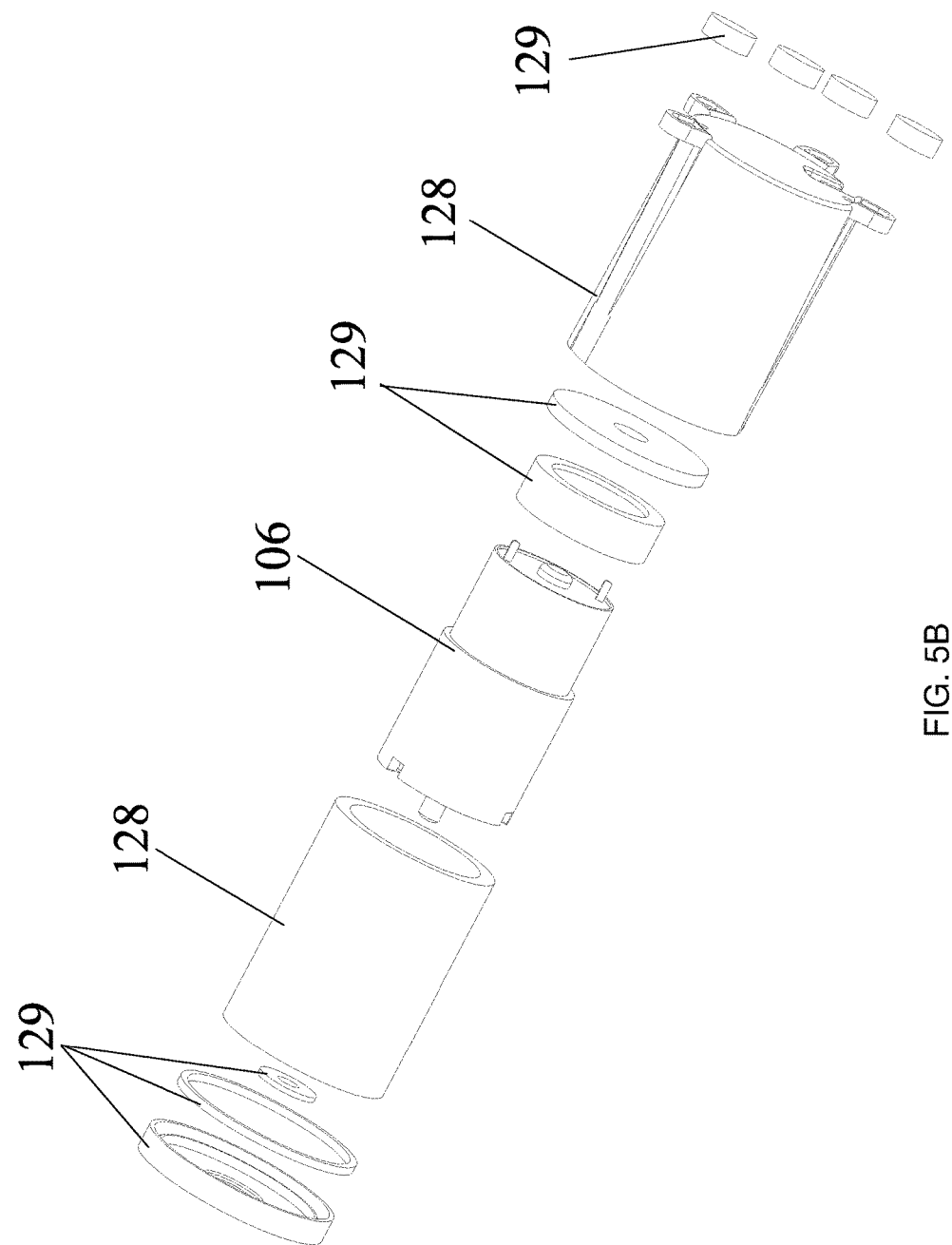
FIG. 5B shows an exploded view of certain components of an imitation candle device in accordance with an exemplary embodiment.
Figure 5C:
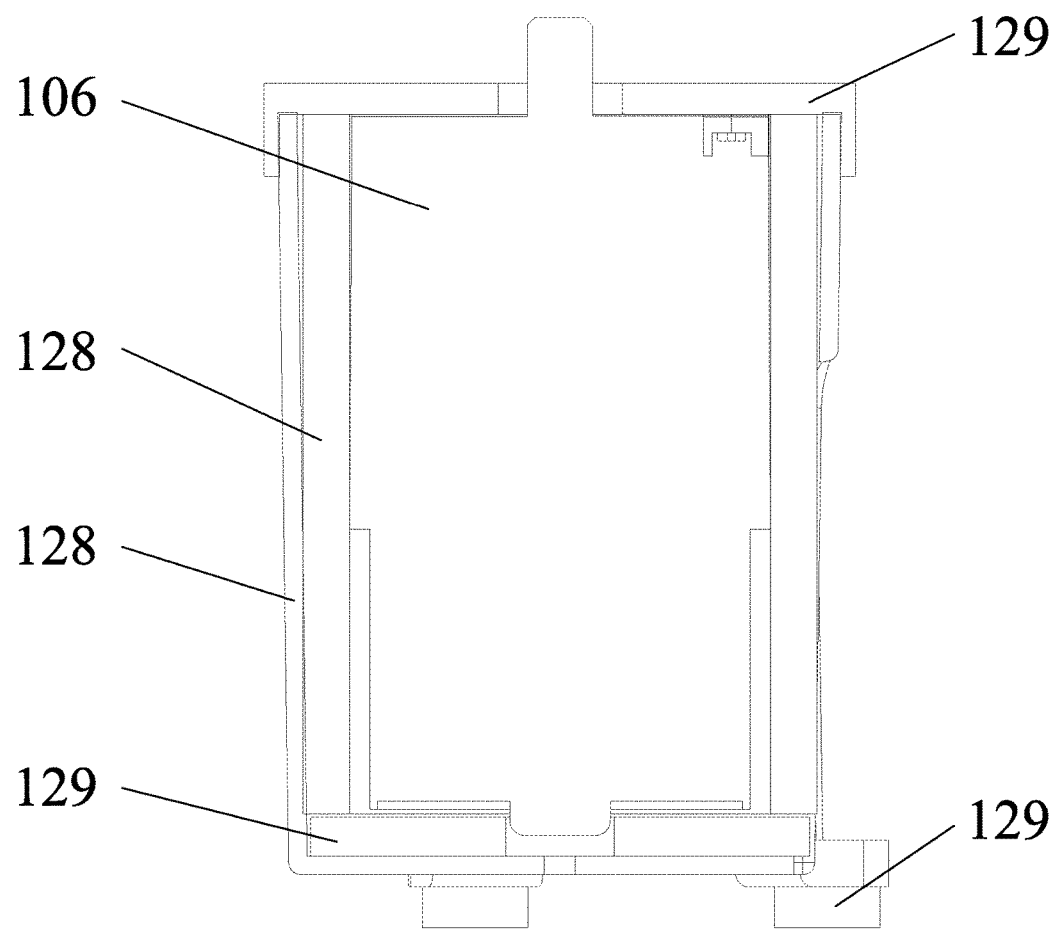
FIG. 5C shows a side view of certain components around an air pump in an imitation candle device in accordance with an exemplary embodiment.

In some embodiments, such as shown in FIGS. 5A-C, the external side of the air pump 106 includes a sound insulation layer 128. The sound insulation layer 128 may be made of sound insulation materials, such as sound insulation cotton, to minimize the noise caused by the air pump 106. For example, the sound insulation material can be sound insulation cotton so that the noise produced by the electronic candle 100 is lower than or equal to 55 dB, or lower than or equal to 45 dB. Within such noise limits, the produced noise has a relatively small impact on the users. In some embodiments, the external side of the air pump 106, including but not limited to the top and/or bottom, may include an anti-vibration component(s) 129 so as to minimize the vibration caused by the air pump 106 in the electronic candle 100, thereby ensuring the stability of electrical contact and visual effect. The material for the anti-vibration component(s) 129 includes, but is not limited to, silica gel and/or rubber. In some implementations, with the anti-vibration component(s) 129, the noise produced by the scent-producing electronic candle 100 is lower than or equal to 55 dB, or lower than or equal to 45 dB. In some embodiments, simultaneous use of sound insulation cotton and an anti-vibration component(s) lowers the noise produced by the electronic candle 100. In some embodiments, the air pump 106 and the fragrance container 107 are positioned in different chambers of the candle device 100 respectively to avoid severe vibration caused by resonance of the air pump 106 and the fragrance container 107, thereby reducing the vibration and noise of the product and reducing disruption to the atmosphere.

In some embodiments, as shown in FIGS. 2A-B, the scent chamber 105 comprises an opening coupled to one end of the second channel 109. In some embodiments, the dimension of the opening of the second channel 109 in the scent chamber 105 is smaller than the dimension of the second channel 109 outside of the scent chamber 105. The shape of the opening includes, but is not limited to, an evenly tapered cone, or a tapered extension in a cylindrical shape, such that the liquid input from the second channel 109 into the scent chamber 105 has a further increased velocity when it leaves the end opening of the second channel 109. In some implementations, the output end opening of the second channel 109 is close to the output end opening of the third channel 110. As a result, the fragrance output via the second channel 109 is fully atomized by the air flow from the third channel 110, and can be extensively distributed in the scent chamber 105.

When the fragrance is a liquid with relatively high viscosity, such as an essential oil, the liquid tends to adhere to the wall of the channel. As time passes by, the path for the scent to flow may become increasingly narrow, which affects scent-producing efficiency. In some embodiments, as shown in FIG. 2C, the internal bottom surface of the scent chamber 105 is not set to be a horizontal plane, but a surface inclined towards the inlet of the first channel 108 so as to form a funnel shape near the inlet of the first channel 108. This way, the liquid fragrance suspended on the inner wall of the scent chamber 105 can return into the fragrance container 107, thereby saving the fragrance. Therefore, the high-velocity air flow can fully atomize the fragrance in the embodiments in accordance with the techniques disclosed herein. Moreover, the fragrance that is not fully atomized may stay on the inner wall of the scent chamber 105 and ultimately flow back into the fragrance container.

Figure 2D:
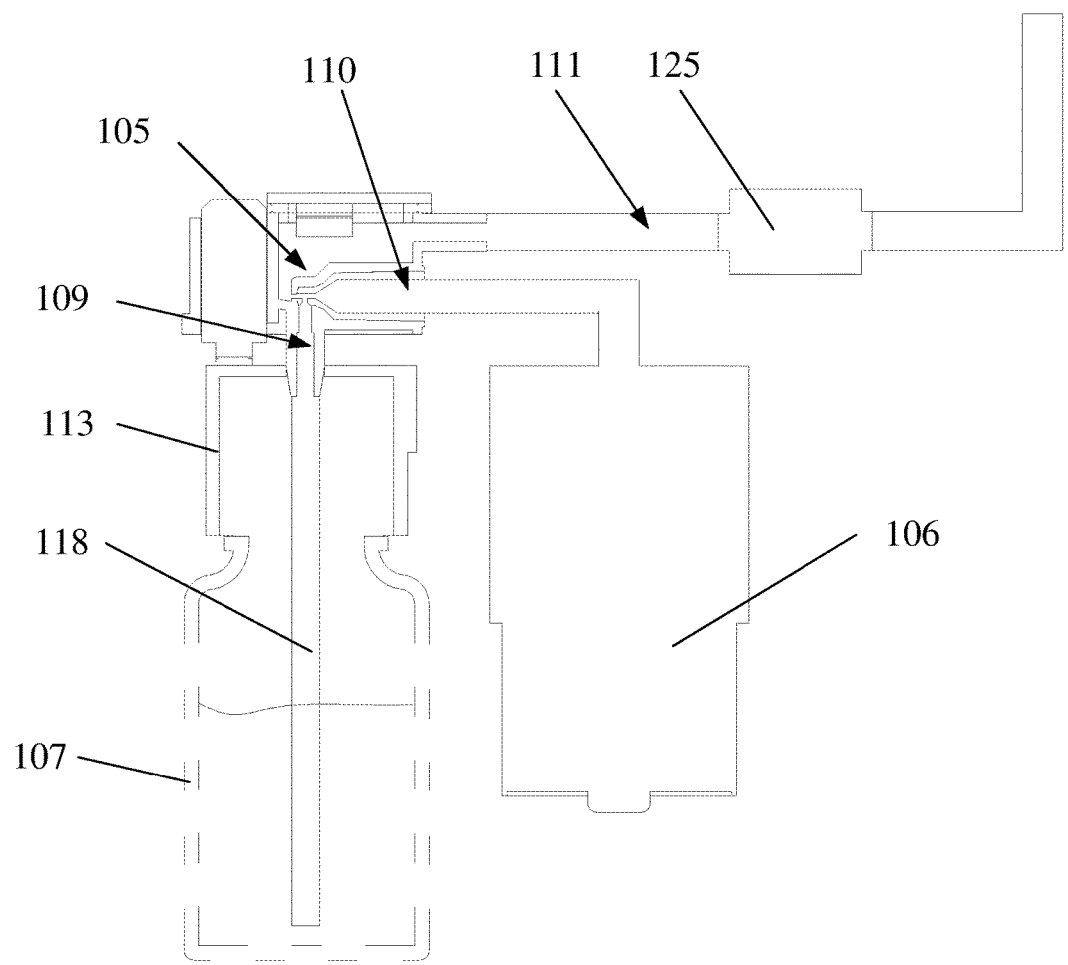
FIG. 2D shows certain components of a scent-producing mechanism within an imitation candle device including a scent chamber, an air pump, and a check valve in accordance with an exemplary embodiment.

In some embodiments, referring to FIG. 2D, the path of the fourth channel 111 includes a check valve 125. In some embodiments, the candle device further includes an inclination sensor 124, as shown in FIG. 4. When the candle device is tilted, the inclination sensor 124 can sense the tilt and then shut down the power supply to the air pump 106. The air pressure in the scent chamber 105 then quickly decreases to shut down the check valve 125.

When the candle device is tilted or inverted, it is possible for the liquid fragrance to flow into the scent chamber 105 through the first channel 108, the second channel 109, the fifth channel 115, the sixth channel 116, and the suction tube 118. The scent chamber 105 acts as a buffer between other channels (e.g., the first channel 108, etc.) and the fourth channel 111 such that the liquid fragrance needs to be accumulated to a certain amount in the scent chamber 105 before it can enter the fourth channel 111 and flow out, which requires the candle device to be tilted or inverted for a relatively long time. In some embodiments, the check valve 125, such as the one shown in FIG. 2D, can stop the fragrance that flows into the fourth channel 111 from leaking out. Furthermore, when the air pump 106 is turned off, the check valve 125 is in a closed state to form a sealed space inside of the fourth channel 111. Therefore, even when the fragrance is in contact with an external channel, the check valve 125 ensures that the fragrance will not flow out of the device. In some embodiments, the inclination sensor 124 may include a rolling ball switch, which can be disposed on a circuit board of the candle device or any other places where it can be positioned. The switch of the inclination sensor 124 can turn on or off the power supply to the air pump 106, either by hardware circuitry or software control. In some embodiments, an inclination angle threshold can be set at, for example, 45 degrees, 75 degrees, or another angle, as the threshold angle formed between the longitudinal axis of the candle device and the vertical axis with respect to the horizon. The threshold can be used to determine when the inclination sensor 124 should shut down the power supply to the air pump 106. For example, as shown in the embodiment in FIG. 4, three inclination sensors 124 are disposed in a triangular manner with respective to each other on a circuit broad. An inclination angle threshold of 45 degrees or 75 degrees is used such that, when the longitudinal axis of the candle device forms an angle, relative to the vertical axis, that is larger than the threshold, the power supply to the air pump 106 is shut down.

Figure 3A:
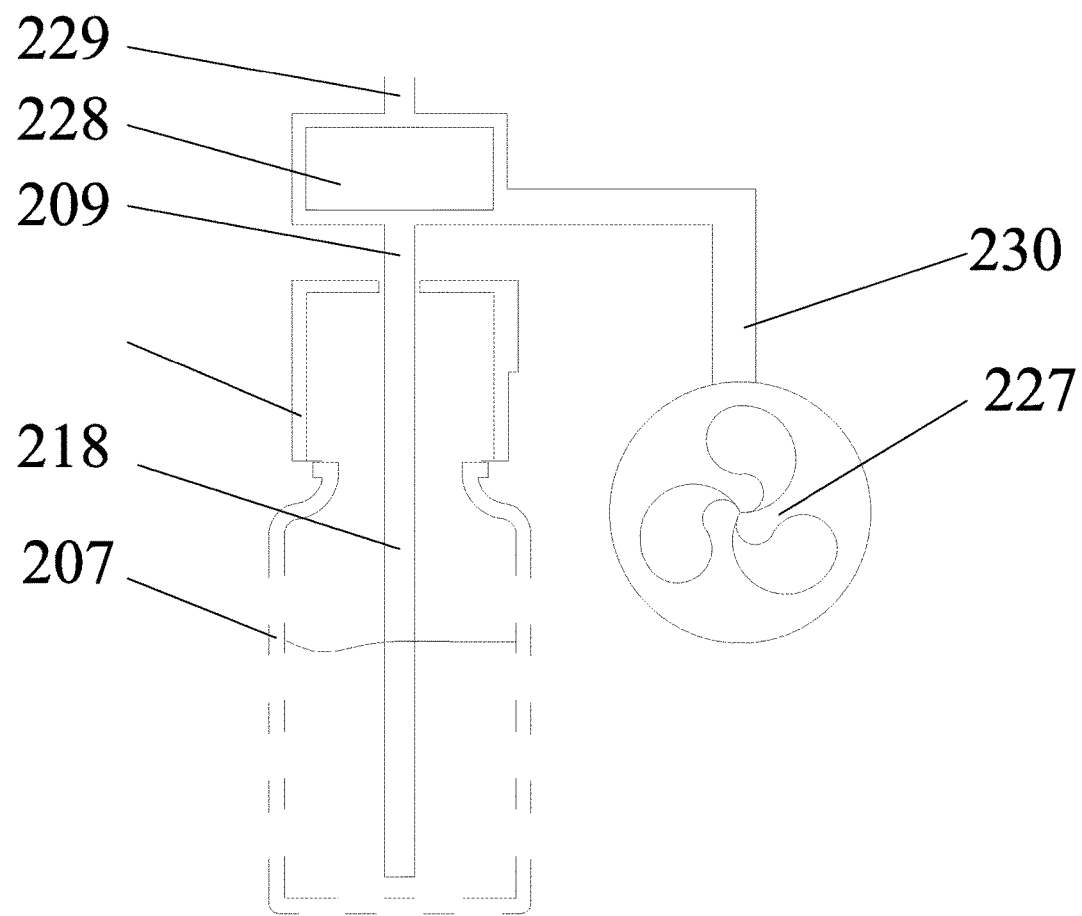
FIG. 3A shows certain components of a scent-producing mechanism within an imitation candle device including a scent chamber and a fan in accordance with an exemplary embodiment.

In some embodiments, referring to FIG. 3A, the candle device does not include a first channel. Instead, the fragrance goes through the suction tube 218 and a corresponding second channel 209 into the scent chamber 105 directly. In some embodiments, the scent chamber may include, or can be replaced by, a water-absorbing material 228 at the location where the suction tube 218, the scent-releasing opening 229, and the seventh channel 230 meet. The water-absorbing material 228 can be used for transporting the liquid fragrance in the fragrance container 207 to an external environment of the candle device. The water-absorbing material 228 includes, but is not limited to, cotton, sponge, etc. The water-absorbing material 228 absorbs the liquid fragrance and helps it evaporate into the air. In the embodiment shown in FIG. 3A, a fan 227 is used to accelerate the evaporation of the fragrance. In some embodiments, the air pump 206 may also be used to accelerate the evaporation of the fragrance. Such embodiments as shown in FIG. 3A require fewer components, thereby allowing the candle device to be smaller and more compact.

Figure 3B:
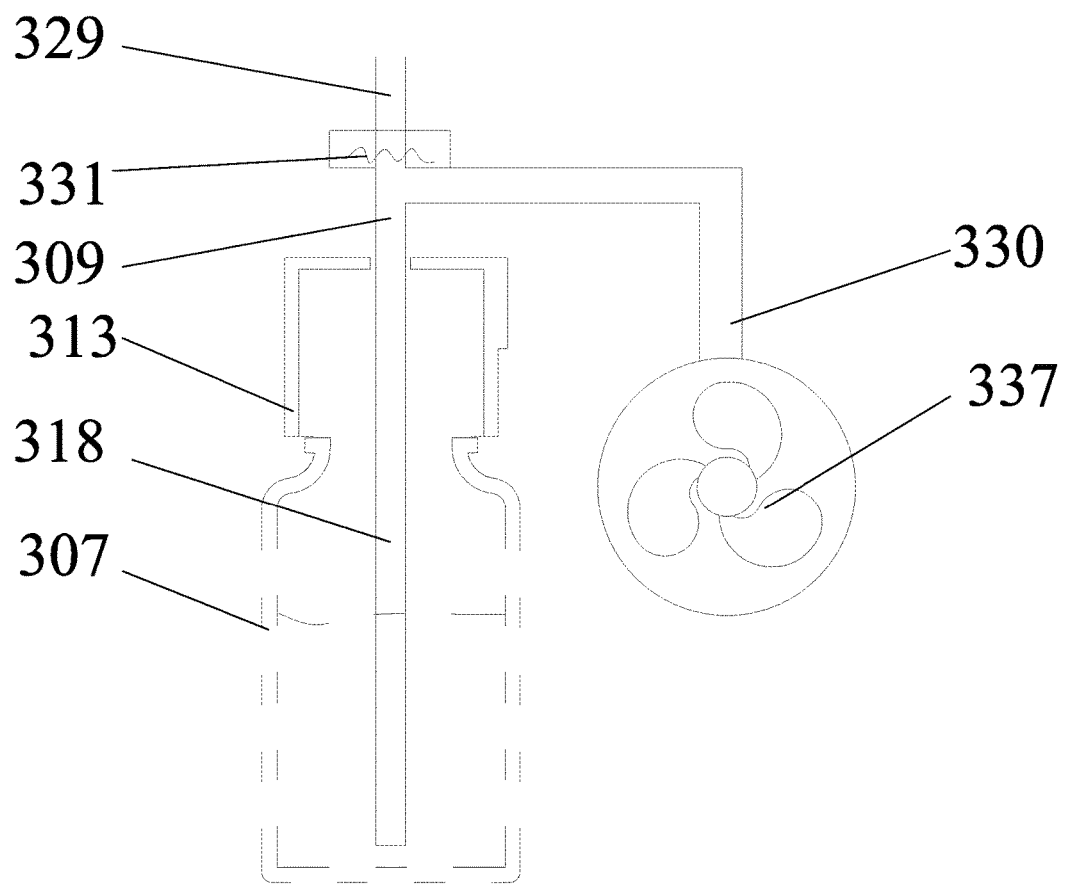
FIG. 3B shows certain components of a scent-producing mechanism within an imitation candle device including a heating device and a fan in accordance with an exemplary embodiment.
Figure 3C:
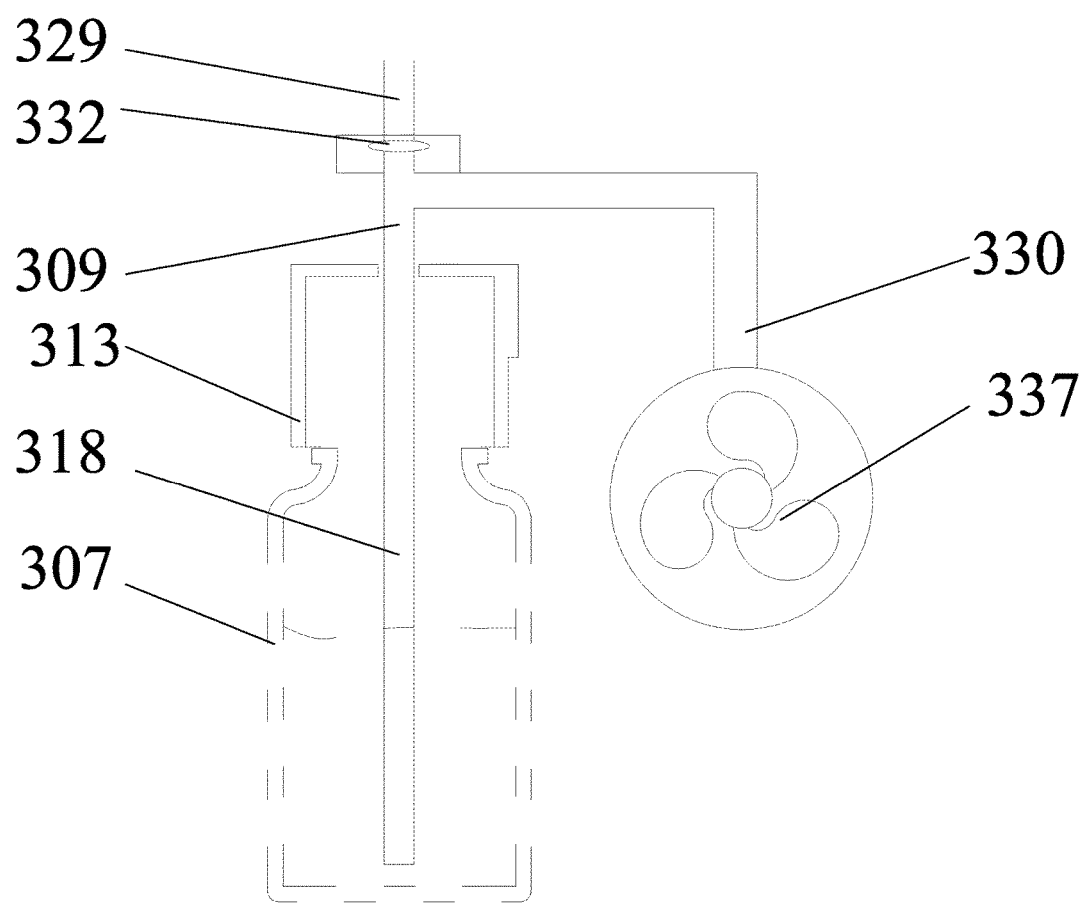
FIG. 3C shows certain components of a scent-producing mechanism within an imitation candle device including an atomizing device and a fan in accordance with an exemplary embodiment.
Figure 3D:
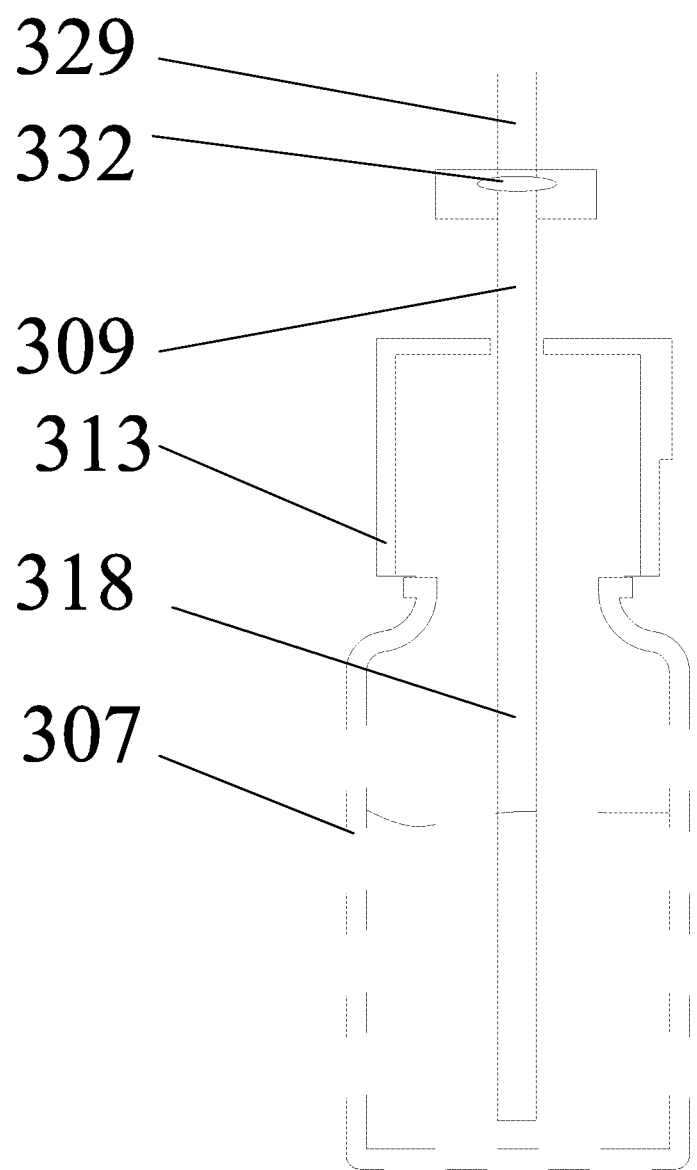
FIG. 3D shows certain components of a scent-producing mechanism within an imitation candle device including an atomizing device in accordance with an exemplary embodiment.

In some embodiments, referring to FIGS. 3B-D, the candle device does not include a first channel. Instead, the fragrance goes through the suction tube 318 and/or a corresponding second channel 309 into the scent chamber directly. In some embodiments, the scent chamber may be replaced by a heating device 331 or an atomizing device 332 at the location where the suction tube 318, the scent-releasing opening 328, and the seventh channel 330 meet. The heating device 331 or the atomizing device 332 can be used for transporting the liquid fragrance in the fragrance container 307 to an external environment of the candle device. In the embodiments shown in FIGS. 3B-3C, a fan 327 is used to accelerate the evaporation of the scent. In some embodiments, as shown in FIG. 3B, the heating device 331 heats and helps the fragrance to evaporate. The heat facilitates the fragrance to evaporate more quickly and evenly. In some embodiments, the heating device 331 may also produce smoke during the process of heating, mimicking a visual effect of a real flame. The heating device 331 may include an electric heating wire, a Positive Temperature Coefficient (PTC) heating element, a semiconductor or electromagnetic heating module, and other electric heating elements.

In some embodiments, as shown in FIG. 4, the electronic candle 100 further comprises a smoke generator 131. The smoke generator 131 is used to further atomize the fragrance and/or additional liquid scent to a smoke. For example, the smoke generator 131 can be the atomizing device 332 as shown in FIGS. 3C-3D. The smoke generator 131 works with a control circuit 133, and the control circuit 133 can be used to detect actions of a user, such as "blowing off," "turning off fan," or "turning off device." In some implementations, when the electronic candle 100 is turned on, the smoke generator 131 does not produce smoke. When the control circuit 133 detects an action of "blowing off," "turning off fan," or "turning off device," the control circuit 133 sends a signal to the control circuitry 132, which controls, according to the signal, the smoke generator 131 to produce smoke when the electronic candle 100 is "extinguished" to simulate the smoke produced when a real candle is extinguished. In some implementations, the smoke generator 131 may also continuously produce smoke when the electronic candle 100 is turned on so that, when the electronic candle 100 is lit, a scent is released and accompanied by a smoke to simulate the smoke produced when a real candle is burning. In some embodiments, the smoke (e.g. a thin smoke) produced by the smoke generator 131 is released from the through hole 102. In some implementations, the shell 101 includes a plurality of holes to allow the smoke to be released.

In some embodiments, the smoke generator 131 is electrically coupled to the control circuitry 132 to control the smoke generator 131. In some embodiments, the smoke generator 131 is an ultrasonic atomizer. After being activated by an electric signal, the ultrasonic atomizer produces high-frequency harmonic oscillations, which cause a porous metal membrane adhered to the ultrasonic atomization piece to produce ultrasonic vibration through energy transfer, causing the liquid adsorbed to the metal membrane to be atomized. Such smoke generator 131 does not require heating or adding a chemical reagent, and thus can be more energy-efficient than atomization techniques that use heat. Such smoke generator 131 also has characteristics such as low noise, long service life, and low power consumption. The smoke produced by the smoke generator 131 may appear like real smoke from a real candle. It is noted that the smoke generator 131 can be implemented using other compatible smoke generation structures and techniques that operate based pressurized atomization, static atomization, ultrasonic atomization, bubble atomization, rotary atomization, annular hole atomization, etc.

Figure 12A:
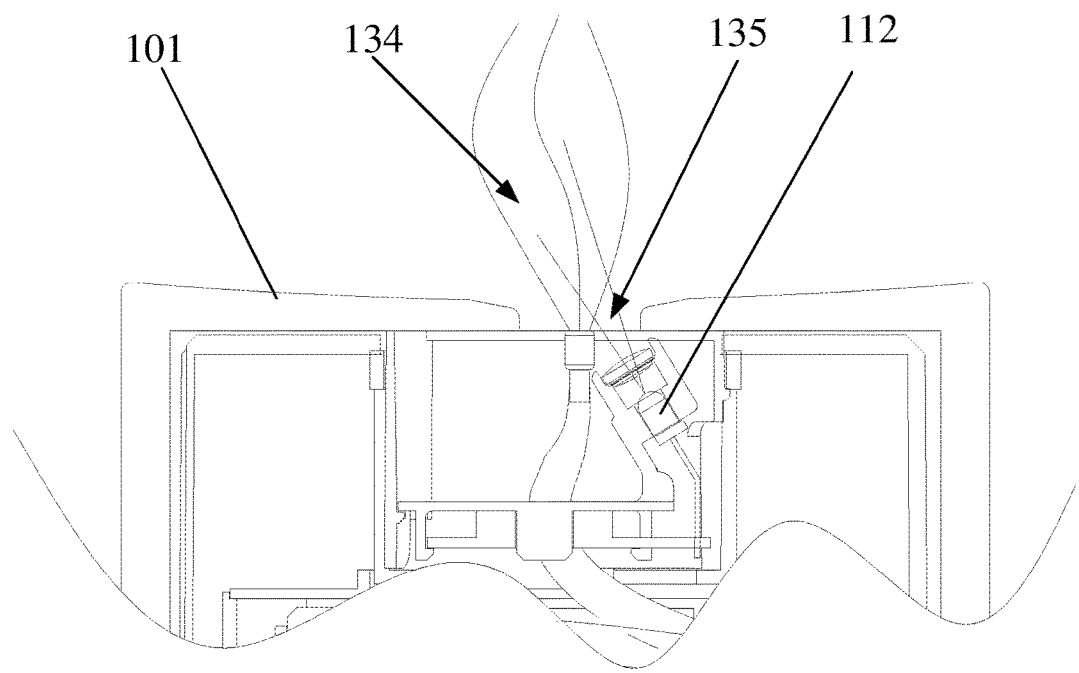
FIG. 12A shows an arrangement of a light-emitting component and scent released in the form of smoke in accordance with an exemplary embodiment.
Figure 12B:
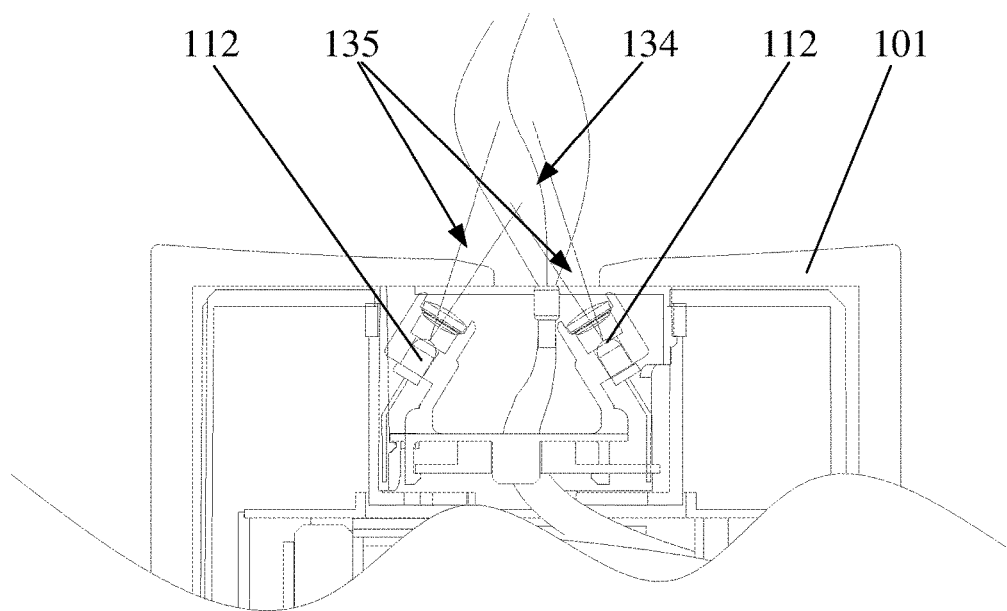
FIG. 12B shows an arrangement of a light-emitting component and scent released in the form of smoke in accordance with an exemplary embodiment.
Figure 12C:
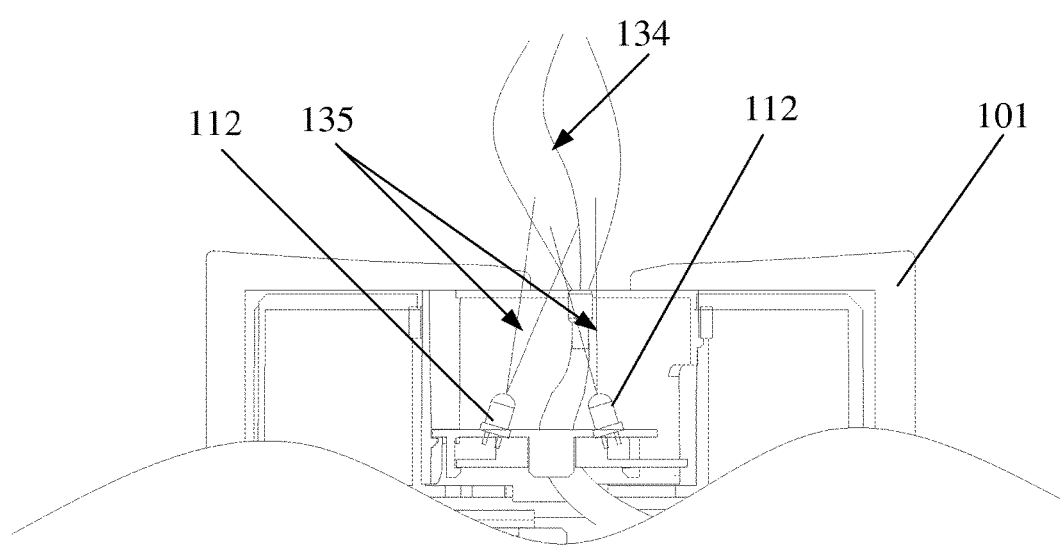
FIG. 12C shows an arrangement of a light-emitting component and scent released in the form of smoke in accordance with an exemplary embodiment.

In some embodiments, the light-emitting element 112 of the electronic candle 100 may be an LED lamp. FIGS. 12A-12C show some embodiments in which the light emitted by at least one LED lamp illuminates the smoke produced during the heating process through a through hole. In some embodiments, the smoke can be blown out of the candle device through the through hole by the air pump or the fan. The illumination of the LED light cast on changing shapes of the smoke can make the flames look like real flames of a burning candle. In some embodiments, the LED light may be installed on one side of the flame element 103, such as shown in FIG. 12A. In some embodiments, the LED light may be installed on two sides of the flame element 103, such as shown in FIG. 12B. In some embodiments, the LED light may be installed on the bottom of a support structure that supports the flame element 103, such as shown in FIG. 12C. The light-emitting element 112 may also be a halogen lamp, which can facilitate the evaporation of the fragrance by the heat of the lamp itself. The warm color of the halogen lamp and the heated smoke give the candle device a more appealing appearance of a real burning candle. In some embodiments, such as shown in FIG. 3C, the atomizing device 332 atomizes the fragrance, which is blown out by the air pump or the fan 337 such that the fragrance can evaporate more evenly. In another embodiment, as shown in FIG. 3C, the atomizing device 332 directly atomizes the fragrance, which is released into the external environment by the scent-releasing opening. Embodiments such as the one shown in FIG. 3C require fewer components so that the candle device can be made smaller and more compact.

Figure 9A:
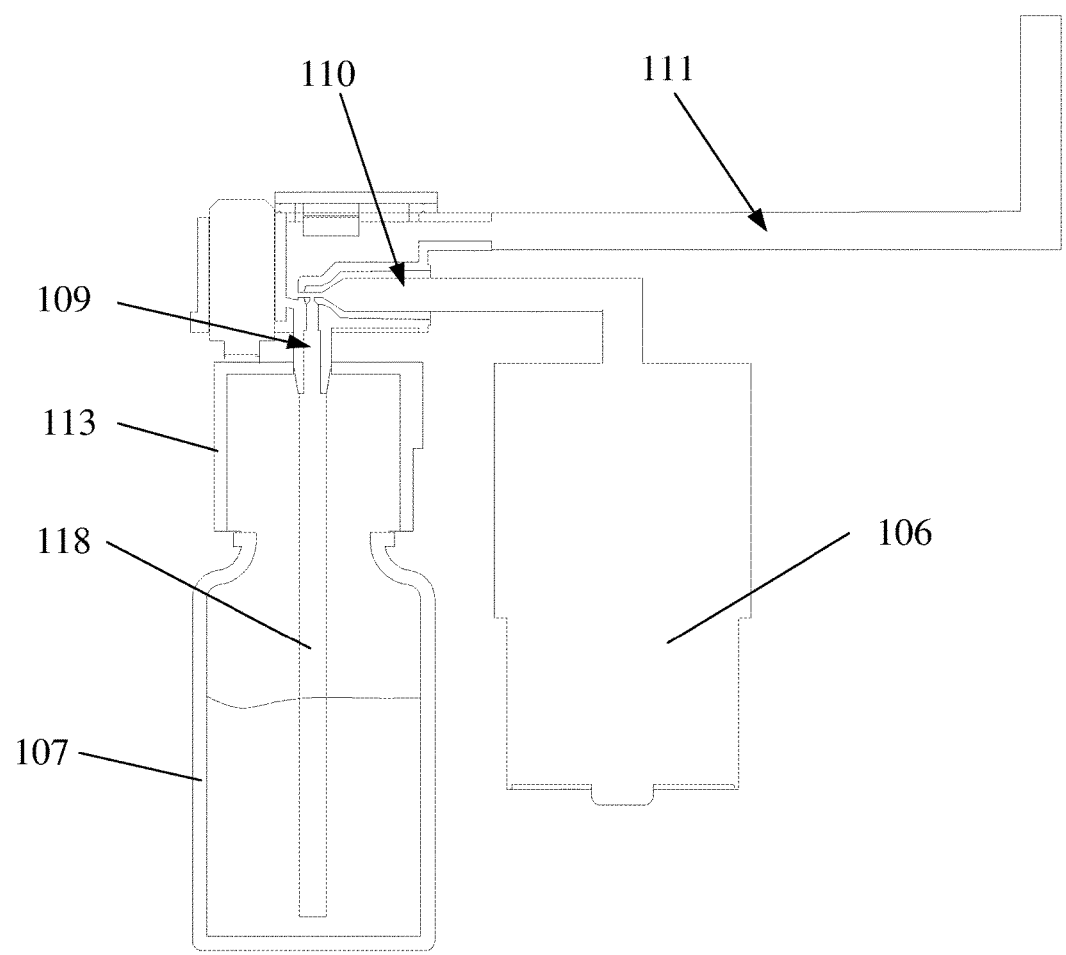
FIG. 9A shows certain components of a scent-producing mechanism within an imitation candle device including a fragrance container, a scent chamber, and an air pump in accordance with an exemplary embodiment.
Figure 9B:
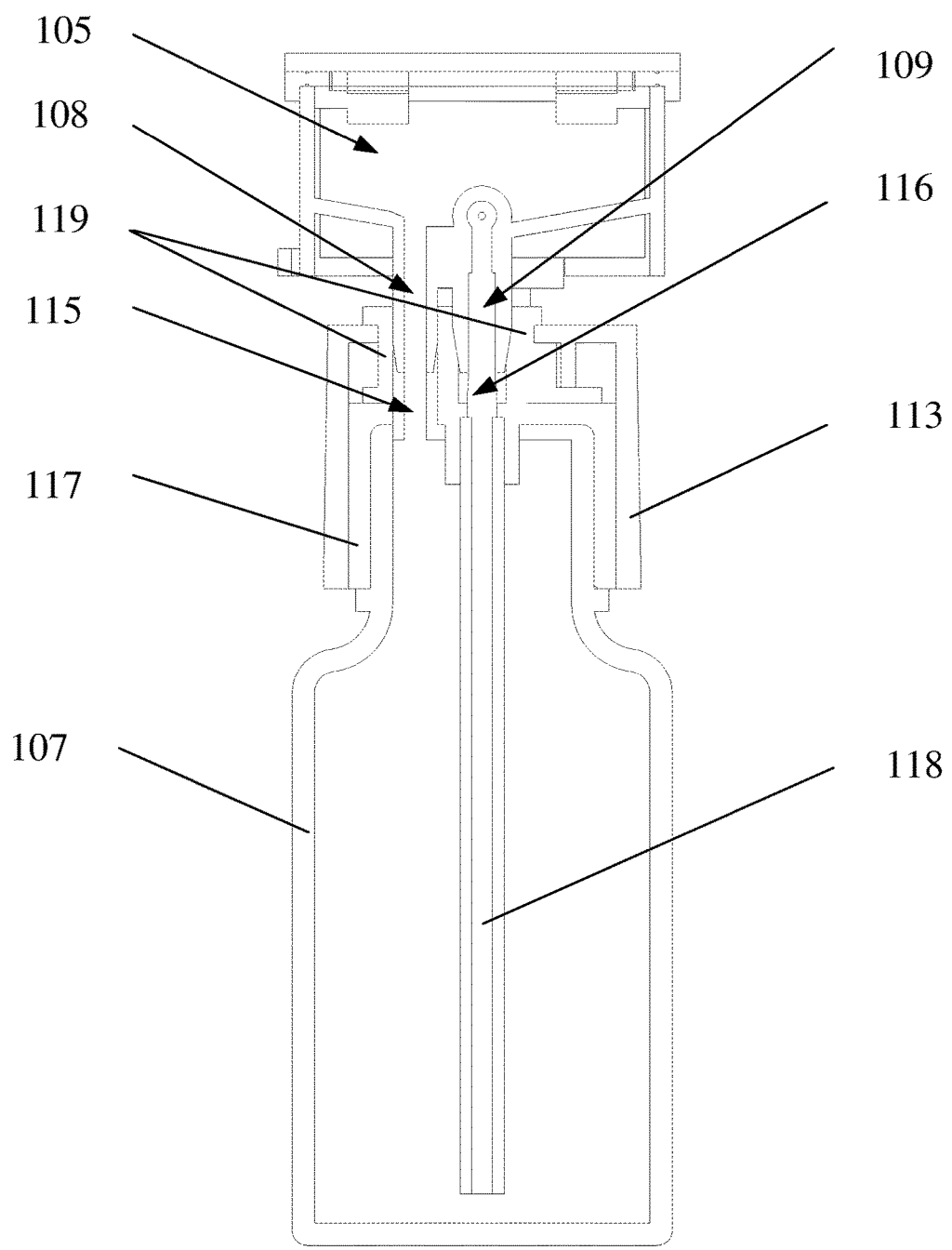
FIG. 9B shows certain components of a scent-producing mechanism within an imitation candle device including a fragrance container and a scent chamber in accordance with an exemplary embodiment.

In some embodiments, referring to FIGS. 9A-9B, the scent-producing candle device includes a fragrance container 107, a first channel 108 coupled to an air inside the fragrance container 107, and a second channel 109 coupled to a fragrance inside the fragrance container 107. The fragrance container 107 can be a bottle containing a liquid fragrance, such as perfume or essential oil. In some embodiments, the air pump 106 pumps air into the scent chamber 105 via the third channel 110.

Figure 13:
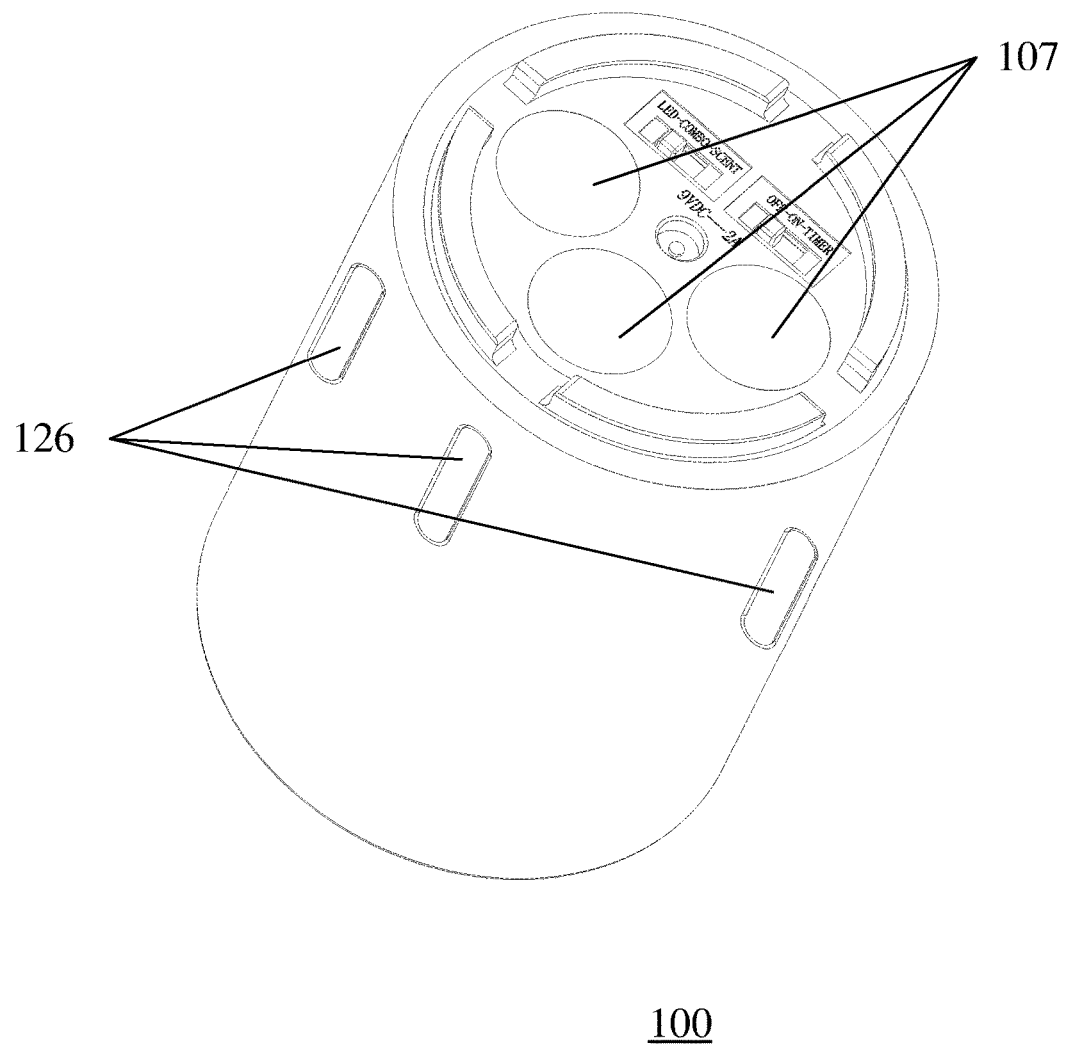
FIG. 13 shows a candle device that includes three fragrance containers in accordance with an exemplary embodiment.

It should be noted the examples described herein include one fragrance container 107 in the scent-producing electronic candle. However, a plurality of fragrance containers 107, for example two, three or more fragrance containers 107, can be used if desired. FIG. 13 shows an example of a candle device that includes three fragrance containers 107. In some implementations, a plurality of scent chambers can be used so that each scent chamber is connected to each of the plurality of fragrance containers 107. A plurality of fourth channels can be connected to the plurality of scent chambers to allow the scent to be transported to an external environment. In some implementations, one scent chamber is connected to the plurality of fragrance containers 107. Another channel is connected to the scent chamber to allow the fragrance to be transported to the outside. A user may choose his or her favorite customized scent by mixing and matching various fragrance stored in the plurality of fragrance containers. Different scents can either be mixed before being sent to an external environment, or be sent to an external environment and then mixed in the air, both of which can further improve the diversity and the effect of scents.

In some embodiments, referring to FIGS. 10A-10B and FIGS. 11A-11B, an electronic candle 100 includes a shell 101, a through hole 102 on the top of the shell 101, a flame element 103 running through the through hole 102 and extending outwardly from the inside of the through hole 102. The inside of the shell 101 is constructed to accommodate a fragrance container 107, a first channel 108 coupled to the air inside the fragrance container 107, and a second channel 109 coupled to a fragrance inside the fragrance container 107. The shell 101 may be used for installation and fixation of various components inside the electronic candle 100. For example, the shell 101 may be used to support a bracket to hold a light-emitting element and a coil for driving a flame piece to sway.

Figure 11B:
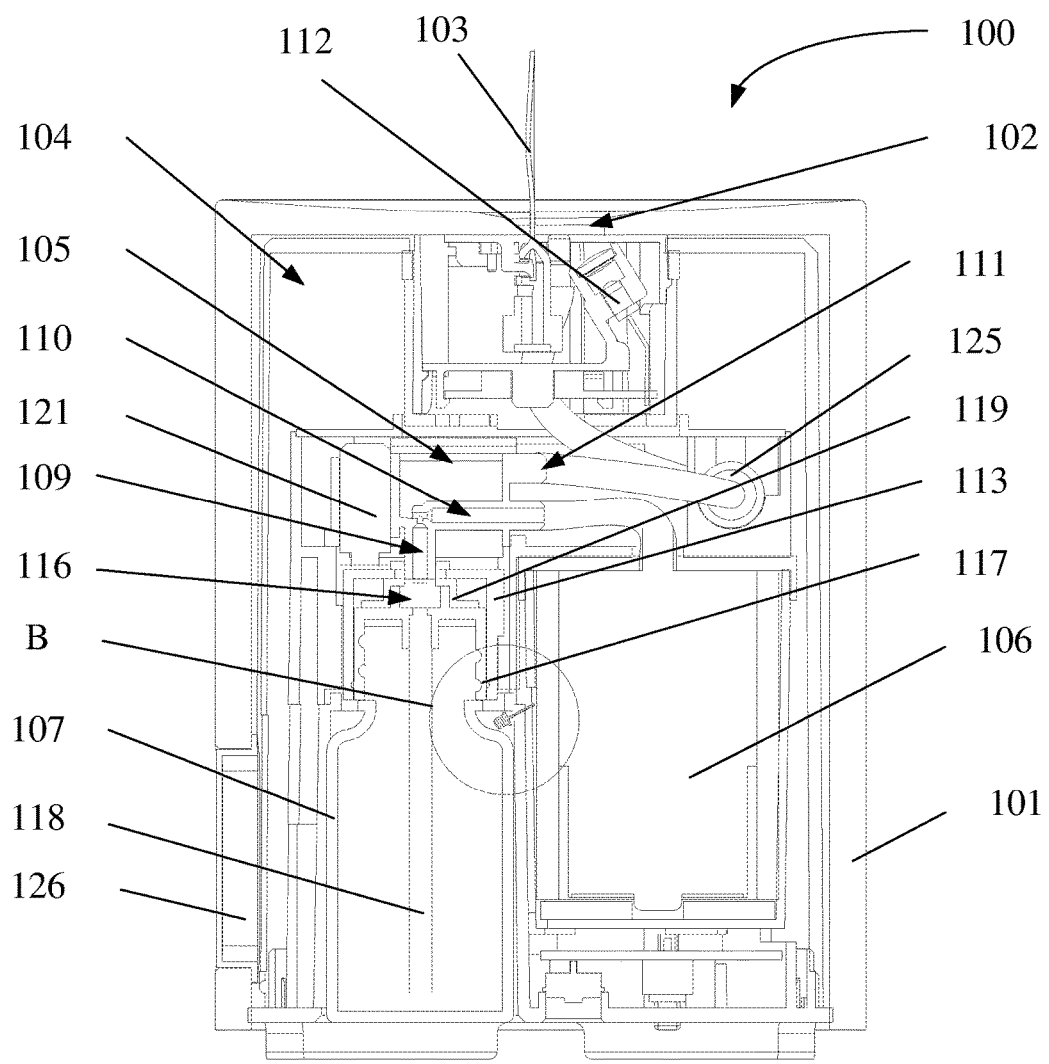
FIG. 11B shows certain components of another electronic imitation candle in accordance with an exemplary embodiment.

In the specific embodiment shown in FIGS. 11A-11B, the candle device 100 includes an accommodating chamber 104 within the shell 101. The scent-producing mechanism includes a scent chamber 105. The scent chamber 105 further includes a first channel (not shown) and a second channel 109. The first channel is constructed to be coupled to the air inside a fragrance container 107, and the second channel 109 is constructed to be coupled to a fragrance inside the fragrance container 107. The scent chamber 105 may also include a third channel 110 and a fourth channel 111. The third channel 110 is constructed to input the air to the scent chamber 105, and the fourth channel is constructed to output a scent produced in the scent chamber 105 to the outside of the electronic candle 100. The fragrance container 107 located within the accommodating chamber 104 can be a bottle containing a liquid fragrance, such as perfume or essential oil. In some embodiments, the accommodating chamber 104 may also be used to accommodate a container holding a solid fragrance, such as a scent block. In some embodiments, the air pump 106 pumps air into the scent chamber 105 via the third channel 110. The air pump 106 can be disposed inside the shell 101. Alternatively, the air pump 106 may also be disposed outside the shell.

Referring to FIG. 11A, in some embodiments, the air enters the scent chamber 105 via the third channel 110. In some implementations, the air pump 106 pumps the air into the third channel 110 such that the air pressure of the scent chamber 105 keeps on increasing. Under the higher air pressure, the air in the scent chamber 105 then enters the the fragrance container 107 via the first channel 108, causing the air pressure in the fragrance container 107 to increase as well. The fragrance in the fragrance container 107 is then transported under pressure into the scent chamber 105 via the second channel 109 to be fully atomized. Because the air pressure in the scent chamber 105 is also higher than the air pressure of the external environment of the electronic candle 100, the atomized fragrance is released via the fourth channel to the outside of the electronic candle 100. Compared to those embodiments that include a fan to drive the air to produce a scent, the embodiments that use an air pump have the following advantages. First, the electronic candle 100 in accordance with the techniques disclosed herein can effectively drive a fragrance to the second channel 109 inside the electronic candle 100 by the air pressure produced by the air pump 106. Meanwhile, the air pressure of the air pump 106 itself can fully atomize a liquid fragrance, which improves the aromatic effect of the fragrance. The atomized fragrance can also appear as smoke produced when the candle device 100 is "burning." Second, the atomized fragrance is more concentrated as compared to fragrance dispersed using other mechanisms, e.g., a fan. Furthermore, the air pressure produced by the air pump 106 is adjustable, thereby allowing the user to adjust the atomization rate of the fragrance. For example, when a fan is used to drive air flow to disperse the liquid fragrance, the magnitude and direction of its pressure acting on the fragrance may not be precisely controlled even though the wind speed and direction of the fan can be adjusted. The air pump, on the other hand, can apply air pressure of different magnitudes and directions in a relatively precise manner, thereby achieving more effective control by the user. Using the air pump, the atomized fragrance can appear like a smoke that is produced by a real burning candle, achieving a more realist look and feel. In some embodiments, the air pump can pump the fragrance at a higher speed to produce a burst of smoke so that the candle device appears to be extinguished like a real candle.

Figure 10A:
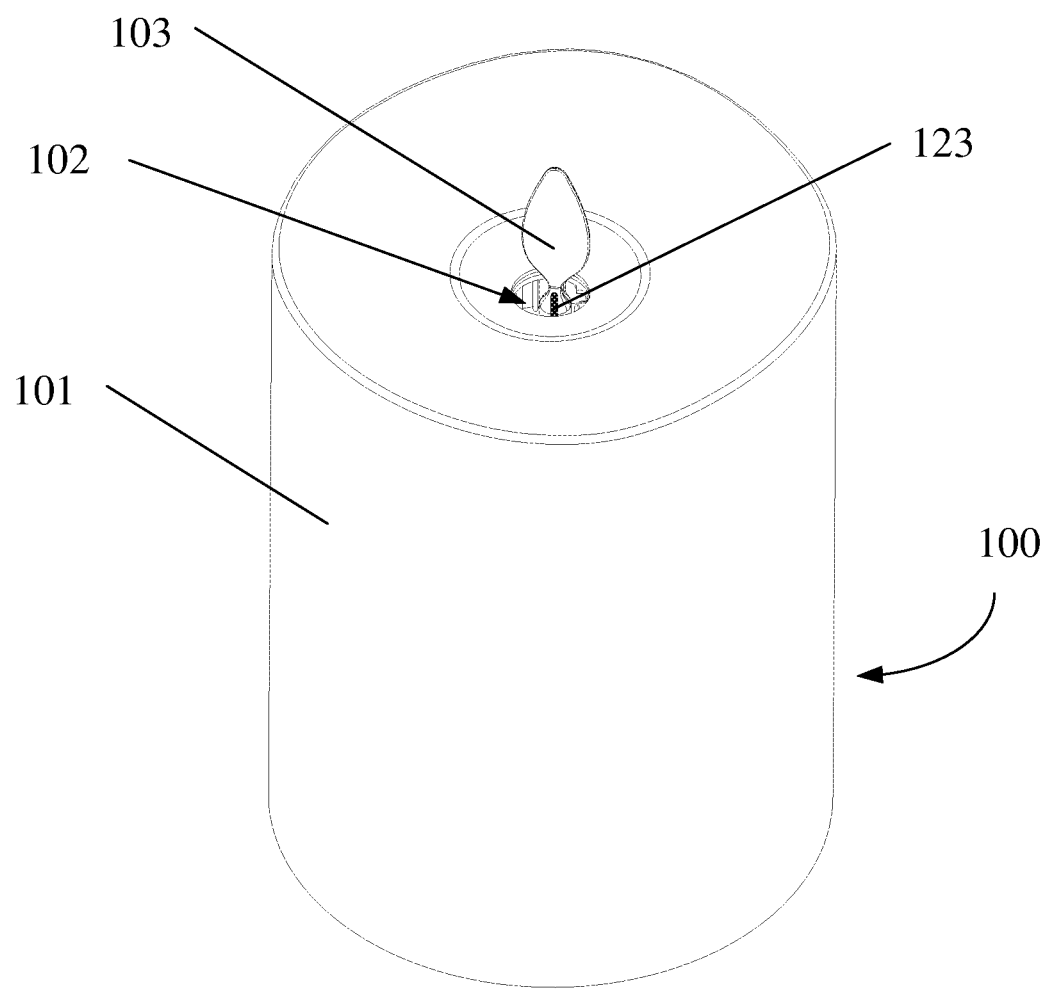
FIG. 10A shows an electronic imitation candle including a flame element in accordance with an exemplary embodiment.
Figure 10B:
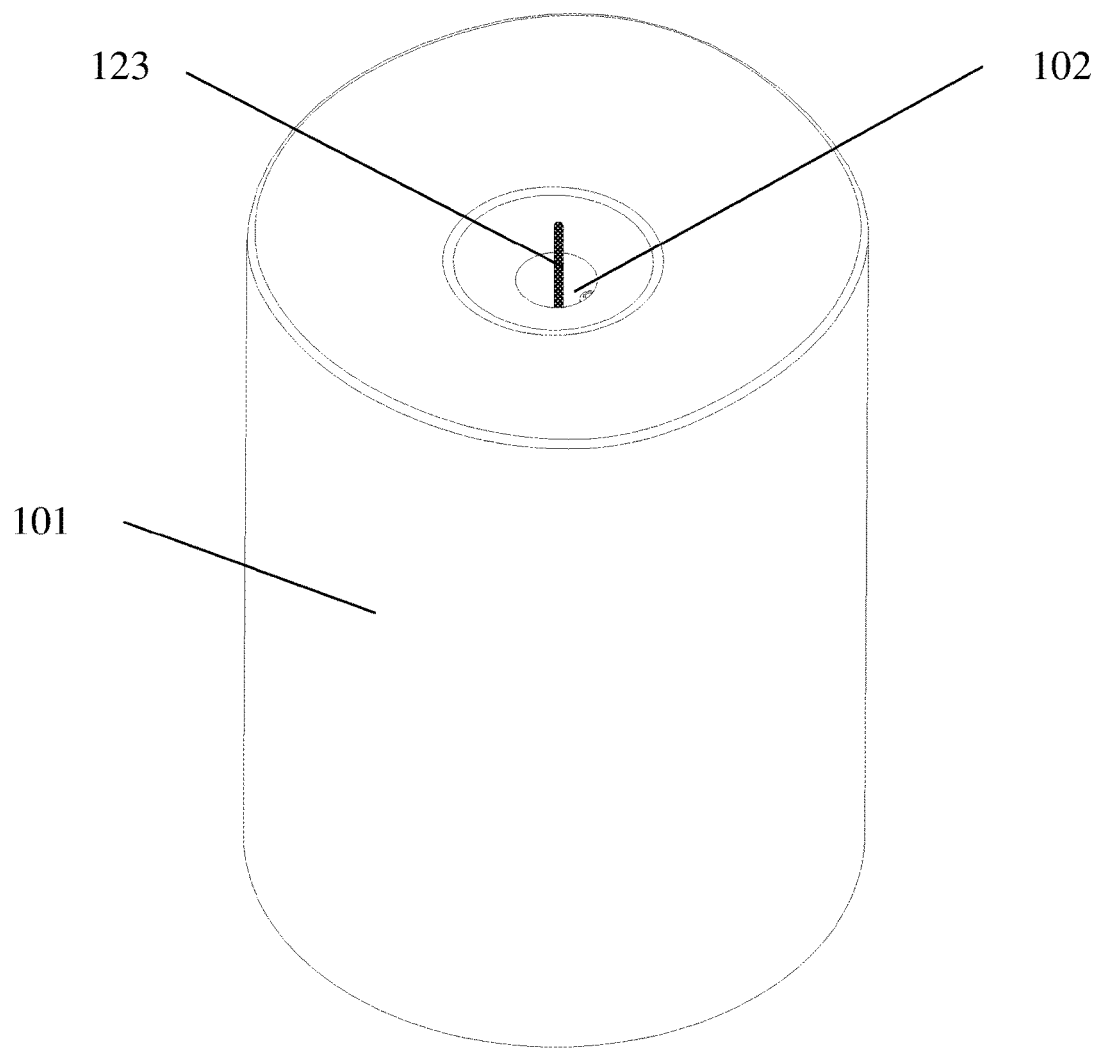
FIG. 10B shows an electronic imitation candle with a retracted flame element and a dark-color component appearing as a wick in accordance with an exemplary embodiment.

In some embodiments, referring to FIGS. 10A-10B, the shell 101 has an appearance similar to a conventional candle. The cross section of the shell 101 may have a triangular, square, oval, or irregular shape. The shell 101 may be made of any one of the materials such as wax, paraffin, plastics, glass, metal, ceramic, crystal, and polymers, or any combination thereof. The top of the shell 101 may be a substantially flat surface, or have a recess, to simulate a brand-new unused candle. The shell 101 may also include additional shapes, such as solidified flows of melted wax, formed on its surface so as to simulate a used candle. The top of the electronic candle 100 includes a through hole 102, and the flame element 103 extends outwardly from inside the shell 101 via the through hole 102.

In some embodiments, the candle device 100 comprises an accommodating chamber 104 and a fragrance container 10 positioned in the accommodating chamber 104. In some embodiments, the fragrance container 107 may pre-installed in the electronic candle 100 during manufacturing or packaging. In some other embodiments, the electronic candle 100 may not carry the fragrance container 107. Instead, a user may install it on his/her own into the accommodating chamber 104 according to his/her preferences of fragrances.

In some embodiments, the accommodating chamber 104 may have a shape of a cuboid or a cube to accommodate a plurality of fragrance containers 107, such as shown in FIG. 13. In some implementations, the accommodating chamber 104 may have a shape of a ring such that the plurality of fragrance containers 107 are evenly or unevenly distributed along the ring-shaped space in the chamber 104.

In some embodiments, one end of the third channel 110 is connected to the scent chamber 105, and the other end of the third channel 110 extends to the through hole 102 to release the scent out of the electronic candle 100. The shell 101 may include a plurality of scent-releasing openings disposed at different positions of the shell. In some embodiments, the other end of the third channel 110 may extend to other places of the electronic candle 100. For example, the electronic candle 100 can be suspended using a support mechanism. The other end of the third channel 100 may extend to the bottom of a electronic candle 100 to release scent from the bottom of the candle. In some embodiments, the support mechanism can be a magnetic levitation mechanism. In some embodiments, one or more additional through hole(s) can be formed at the bottom of the electronic candle to allow convection of the air and the fragrance in the electronic candle 100 to enable a smoother spray of the scent from the electronic candle 100.

In some embodiments, as shown in FIG. 10A, the upper portion of the flame element 103 has a flame shape and can make irregular movements. When a light is projected onto the flame element 103, the flame element 103 randomly sways to simulate of the movements of a real flame. In addition, as shown in FIGS. 10A-10B, the flame element 103 includes a dark-colored section 123 to simulate a real candle wick after burning. As shown in FIG. 4, when the control circuit 133 detects one of the following actions of "blowing off," or "turning off the fan," or "turning off the device", the control circuit 133 sends a signal to the control circuitry 132, which controls the smoke generator 131 according to the signal to produce smoke when the electronic candle is extinguished to simulate the smoke produced when a real candle is extinguished. At the same time, the flame element 103 may retract, as shown in FIGS. 10A-10B, and the dark-colored section 123 of the flame element 103 extends outside of the through hole 102 to simulate a real candle wick after burning. The dark-colored section 123 may still remain outside of the through hole 102, and/or may slightly rise outside of the through hole 102. The flame shape on the upper portion of the flame element 103 can be a sheet-like flame, or may be combined by two or more sheet-like flames, or may have a 3D shape. In some embodiments, the flame element 103 may be made of plastic or an organic synthetic material. In some embodiments, the flame element 103 is made of a translucent material, such that the flame can be seen from both sides of the flame piece. In some implementations, the flame piece on the upper portion of the flame element 103 has an uneven thickness to simulate lighting effects of a flame at different heights. For example, the flame piece is thin at the top and thick at the bottom. For another example, the flame piece is thin at the top, thick in the middle, and thin at the bottom. In some embodiments, the flame element 103 includes a pivot hole (not shown). A support element, e.g., a rigid V-shaped rod, goes through the pivot hole to support the flame element 103. In some implementations, the distances between the lowest point of the support element and two ends are not equal. The light source 112 can be positioned at the end that has a shorter distance to allow better illumination of the flame-shaped portion. The support element may be a soft wire, and two ends of the support element can be fixed to the shell 101 such that the flame element 103 can pivot about the support element. In some embodiments, the lower portion of the flame element 103 may have a magnet or a magnetic material, such that the flame element can make nonlinear movements varying with time under the action of the magnetic field. In some embodiments, the flame element 103 is driven by other mechanisms such as air flow (e.g., from a fan) or gas flow from the outside.

Moreover, as shown in FIG. 4, the electronic candle 100 further comprises a remote control module 136. A user can send an electric signal to the remote control module 136 using a remote control device. The remote control module 136 receives the electric signal and sends a signal to the control circuitry 132, and the control circuitry 132 controls, according to the signal, the electronic candle 100 to turn the electronic candle 100 on or off and to perform other controls of the device.

To enable the air pump 106 and the light-emitting element 112 to operate normally, the electronic candle 100 further comprises a power supply. The power supply may be formed by providing a battery chamber to accommodate one or more dry cells or re-chargeable batteries. In the case of a rechargeable battery, the battery can be charged in a wired charging mode. In some embodiments, the power supply may also be charged in a wireless charging mode. In some implementations, the power supply may be charged with solar energy; such solar energy is converted into electrical energy for storage when the product is not in use, and the electrical energy can be supplied to the electronic candle 100 during use. In some embodiments, the power supply may include a plug that is directly connected to an AC outlet so as to supply power to the electronic candle 100.

Furthermore, as shown in FIGS. 14A-14D, the bottom of the electronic candle 100 includes a plurality of support components 128 (e.g., legs). The plurality of support components 128 are separated from one another by corresponding gaps. As shown in FIG. 14D, a power supply connection 129 is formed in the center bottom of the electronic candle 100, where a can be connected to the power supply connection 129. The spacing between the support components 128 allows the power cord to reach the electronic candle while the electronic candle is placed on a flat surface. The user may select, according to the desired position and direction of the electronic candle 100, the appropriate gap for routing the power cord.

In some embodiments, referring to FIG. 13 and FIGS. 14A-14D, the shell 101 of the electronic candle 100 includes at least one observation window 126 to observe the remaining quantity of fragrance in the fragrance container 107.

Figure 11C:
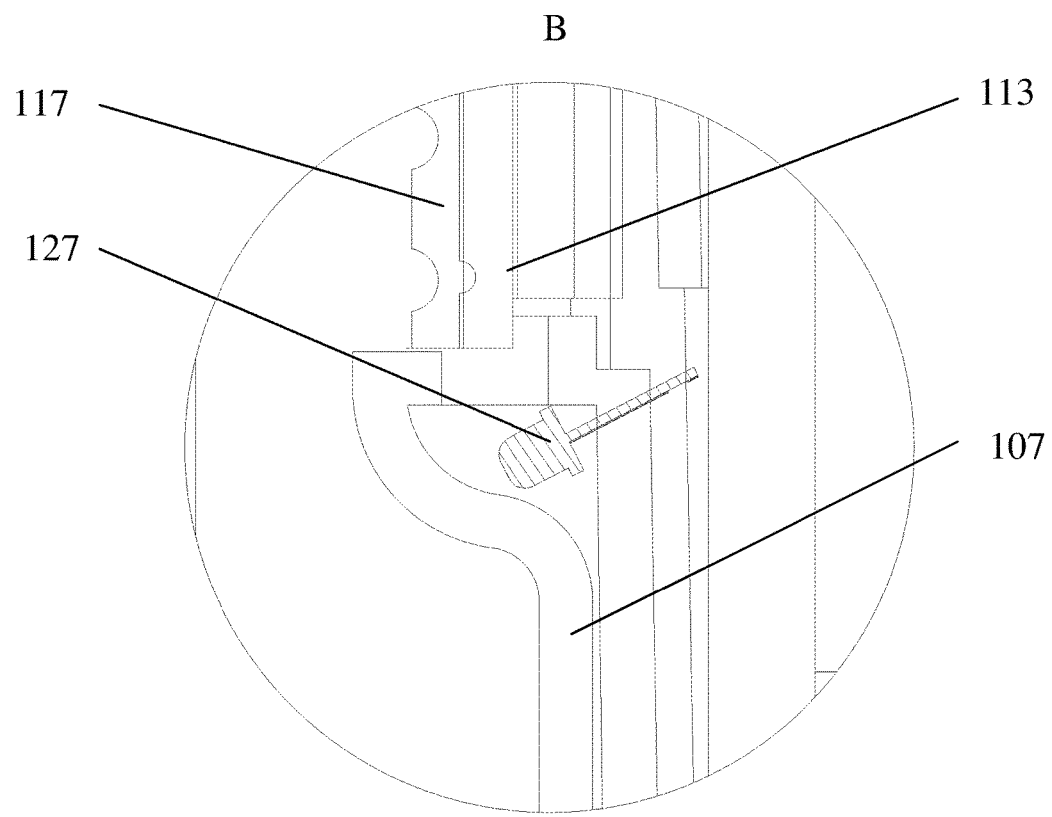
FIG. 11C shows an enlarged detailed view of some of the components in FIG. 11B.

When there is a plurality of fragrance containers 107, the shell 101 includes a plurality of observation windows 126, each corresponding to one of the plurality of fragrance containers 107. In some embodiments, the observation window 126 is made of a clear plastic. In some implementations, the observation window 126 may have a specific shape such as, but not limited to, a rectangle, a rhombus, an ellipse, and the like. To allow the user to observe the fragrance under poor lighting situations, in some embodiments such as shown in FIGS. 11B-11C, a light source 127 may be provided in the electronic candle 100. The light source 127 can illuminate the body of the fragrance container 107 such that the quantity of remaining fragrance can be observed.

It is noted that the fragrance container 107 may hold a liquid fragrance. In some embodiments, the fragrant container may also hold a scented bead, a scented block, etc. In some implementations, the fragrance container 107 may simply contain water. When the water is atomized, it can humidify the air and achieve an effect similar to that of a humidifier.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An electronic candle device, comprising:
   a shell including a through hole;
   a flame element protruding through the through hole;
   an installation lid including a locking base to allow removable coupling of a fragrance container;
   a scent chamber including a locking clip, a first channel, a second channel, a third channel, and a fourth channel, wherein the scent chamber is removably coupled to the locking base by the locking clip; and
   an air pump configured to pump air,
   wherein the first channel of the scent chamber is positioned to direct the pumped air to exit the scent chamber,
   wherein the second channel of the scent chamber is positioned to draw, under air pressure of the pumped air, a fragrance material into the scent chamber,
   wherein the third channel of the scent chamber is coupled to the air pump to allow pumped air to enter the scent chamber, and
   wherein the fourth channel of the scent chamber is coupled to the through hole to allow a fragrance material to reach an external environment of the electronic candle device.

2. The electronic candle device of claim 1, further comprising:
   a fragrance container that is removably connectable to the installation lid,
   wherein the first channel of the scent chamber is removably connectable to a first section of the fragrance container to direct the pumped air into the fragrance container, and
   wherein the second channel of the scent chamber is removably connectable to a second section of the fragrance container to draw the fragrance material from the fragrance container into the scent chamber.

3. The electronic candle device of claim 2, wherein the installation lid includes a protrusion to facilitate correct alignment of the installation lid and the fragrance container.

4. The electronic candle device of claim 3, further comprising an indicator positioned at an external surface of the electronic candle device to indicate a location of the protrusion.

5. The electronic candle device of claim 2, wherein the shell includes an observation window corresponding to the fragrance container for allowing a user to observe a remaining quantity of the fragrance material in the fragrance container.

6. The electronic candle device of claim 5, comprising a light source positioned within the shell, the light source configured to illuminate a fragrance container so that a remaining quantity of a fragrance material in the fragrance container can be observed via the observation window.

7. The electronic candle device of claim 2, comprising a light source positioned in proximity to the through hole,
   wherein the air pomp is configured to pump air at a high pressure to allow the fragrance material in the fragrance container to reach the external environment in a smoke form, and
   wherein the light source is configured to illuminate the flame element and the fragrance material in the smoke form to create an appearance of a real flame.

8. The device of claim 1, further including a fifth channel coupled to the first channel of the scent chamber and a sixth channel coupled to the second channel of the scent chamber.

9. The electronic candle device of claim 8, further including a suction tube coupled to the sixth channel to facilitate drawing of the fragrance material the scent chamber.

10. The electronic candle device of claim 1, wherein the installation lid includes a mount support positioned removably on the installation lid to facilitate coupling of a fragrance container.

11. The electronic candle device of claim 1, Wherein a first end of the second channel that is coupled to the scent chamber has a smaller dimension than a second end of the second channel.

12. The electronic candle device of claim 1, wherein the second channel has a tapered shape.

13. The electronic candle device of claim 1, wherein a bottom surface of the scent chamber has a funnel shape.

14. The electronic candle device of claim 1, comprising:
   a central control circuit,
   a power supply, and one or more tilt sensors, wherein each of the one or more tilt sensors is configured to sense a tilt angle of the electronic candle device, the one or more tilt sensors further configured to transmit a signal to the central control circuit to shut down the power supply upon sensing that the tilt angle is greater than or equal to a predetermined threshold angle.

15. The electronic candle device of claim 14, wherein the predetermined threshold angle is 45 degrees.

16. The electronic candle device of claim 14, comprising a valve coupled to the fourth channel, wherein the valve is configured to, upon receiving a signal from the central control circuit indicative that the tilt angle is greater than or equal to the predetermined threshold angle, close the fourth channel to prevent the fragrance material from spilling outside of the electronic candle device.

17. The electronic candle device of claim 1, comprising a sound insulation layer around the air pump for reducing noise caused by the air pump to lower than or equal to 55 dB.

18. The electronic candle device of claim 1, comprising an anti-vibration component positioned at an external side of the air pump for reducing vibration caused by the air pump.

19. The electronic candle device of claim 1, wherein the flame element is configured to retract into the shell when the electronic candle device is turned off.

20. The electronic candle device of claim 1, comprising a dark-colored component protruding through the through hole, the dark-colored component configured to have an appearance of a wick.

* * * * *